United States Patent
Smith et al.

(10) Patent No.: US 10,782,308 B2
(45) Date of Patent: Sep. 22, 2020

(54) DIRECT READING DETECTION KITS FOR SURFACE CONTAMINATION BY ANTINEOPLASTIC DRUGS

(71) Applicant: The Government of the United States of America as represented by the Secretary of the Department of Health and Human Services, Centers For Disease Control and Prevention, Atlanta, GA (US)

(72) Inventors: Jerome Smith, Cincinnati, OH (US); Deborah Sammons, Cincinnati, OH (US); Shirley Robertson, Cincinnati, OH (US)

(73) Assignee: THE GOVERNMENT OF THE UNITED STATES OF AMERICA AS REPRESENTED BY THE SECRETARY OF THE DEPARTMENT OF HEALTH AND HUMAN SERVICES, CENTERS FOR DISEASE CONTROL AND PREVENTION, Atlanta, GA (US)

( * ) Notice: Subject to any disclaimer, the term of this patent is extended or adjusted under 35 U.S.C. 154(b) by 920 days.

(21) Appl. No.: 13/943,430

(22) Filed: Jul. 16, 2013

(65) Prior Publication Data

US 2014/0017812 A1  Jan. 16, 2014

Related U.S. Application Data

(60) Provisional application No. 61/672,059, filed on Jul. 16, 2012.

(51) Int. Cl.
*G01N 33/558* (2006.01)
*G01N 33/94* (2006.01)

(52) U.S. Cl.
CPC ........... *G01N 33/94* (2013.01); *G01N 33/558* (2013.01)

(58) Field of Classification Search
None
See application file for complete search history.

(56) References Cited

U.S. PATENT DOCUMENTS 5,384,264 A * 1/1995 Chen ................. B01L 3/5023
422/400
5,415,994 A * 5/1995 Imrich ................. B01L 3/5023
435/5

(Continued)

FOREIGN PATENT DOCUMENTS

WO  WO 2006/104970  10/2006
WO  WO-2008/073222  6/2008

OTHER PUBLICATIONS

Chu, W. et al., Pilot assessment of the antineoplastic drug contamination levels in British Columbian hospitals pre- and post-cleaning, *J Oncol Pharm Pract*, 18(1): 46-51, Mar. 2012 EPub Jul. 2011 (Abstract).

(Continued)

*Primary Examiner* — Christopher L Chin
(74) *Attorney, Agent, or Firm* — Knobbe, Martens, Olson & Bear, LLP

(57) ABSTRACT

Methods, kits and devices for detecting antineoplastic drug contamination of a surface are provided according to aspects of the present invention. According to aspects of the invention, methods for detecting antineoplastic drug contamination of a surface include providing a wetting solution compatible with the antineoplastic drug and formulated to promote release of the drug from the surface to be assayed; providing a solid matrix for reversible absorption of the antineoplastic drug; contacting the solid matrix with the wetting solution, generating an assay matrix; contacting the (Continued)

assay matrix and the surface, generating a surface sample; contacting the surface sample with a volume of wetting solution, generating a fluid test sample; and quantifying the antineoplastic drug in the fluid test sample by lateral flow assay to produce an assay result, thereby detecting antineoplastic drug contamination of the surface.

15 Claims, 16 Drawing Sheets

(56) References Cited

U.S. PATENT DOCUMENTS

| | | | |
|---|---|---|---|
| 6,103,536 A * | 8/2000 | Geisberg | G01N 33/54306 422/423 |
| 6,156,271 A * | 12/2000 | May | B01L 3/5023 422/412 |
| 6,663,833 B1 | 12/2003 | Stave et al. | |
| 7,175,993 B2 | 2/2007 | Salamone et al. | |
| 7,459,281 B2 | 12/2008 | Salamone et al. | |
| 7,465,587 B2 | 12/2008 | Imrich | |
| 7,767,794 B2 | 8/2010 | Salamone et al. | |
| 7,901,949 B2 | 3/2011 | Raj | |
| 8,563,264 B2 | 10/2013 | Halverson et al. | |
| 9,766,243 B2 * | 9/2017 | Scheefers | G01N 33/57419 |
| 2004/0033621 A1 * | 2/2004 | Kennedy | G01N 33/558 436/514 |
| 2006/0177883 A1 | 8/2006 | Salamone et al. | |
| 2006/0177884 A1 | 8/2006 | Salamone et al. | |
| 2006/0292700 A1 | 12/2006 | Wang et al. | |
| 2008/0138842 A1 * | 6/2008 | Boehringer | G01N 33/558 435/7.94 |
| 2012/0107956 A1 | 5/2012 | Boehringer et al. | |

OTHER PUBLICATIONS

Hedmer, M. et al., Surface Contamination of Cyclophosphamide Packaging and Surface Contamination with Antineoplastic Drugs in a Hospital Pharmacy in Sweden, *Ann. Occup. Hyg.*, 49(7): 629-37, 2005, Online Aug. 26, 2005.

Hedmer, M. et al., Hygienic guidance values for wipe sampling of antineoplastic drugs in Swedish hospitals, *J Environ Monit*, 14(7): 1968-75, Jun. 27, 2012, EPub Jun. 12, 2012 (Abstract).

Kim, J. et al., Recent advances in rapid and ultrasensitive biosensors for infectious agents: lesson from Bacillus anthracis diagnostic sensors, *Analyst*, 135(6): 1182-90, 2010, Online Mar. 30, 2010.

Kopp, B. et al., Evaluation of working practices and surface contamination with antineoplastic drugs in outpatient oncology health care settings, *International Archives of Occupational and Environmental Health* 86: 47-55, 2013, Online Feb. 5, 2012.

Laderman, E. et al., Rapid, sensitive, and specific lateral-flow immunochromatographic point-of-care device for detection of herpes simplex virus type 2-specific immunoglobulin G antibodies in serum and whole blood, *Clinical and Vaccine Immunology*, 15(1): 159-63, 2008.

Mason, H. et al., Cytotoxic Drug Contamination on the Outside of Vials Delivered to a Hospital Pharmacy, *Am. Occup. Hyg.*, 47(8): 681-85, 2003.

Pretty, J. et al., Sampling and mass spectrometric analytical methods for five antineoplastic drugs in the health care environment, *Journal of Oncology Pharmacy Practice*, 18(1): 23-36, Mar. 2012, Online Dec. 23, 2010.

Salamone, S. et al., Novel monoclonal antibodies for measuring 5-fluorouracil concentrations in biological fluids, *Journal of Clinical Oncology*, 24(18S): 2055, 2006 ASCO Annual Meeting Proceedings, 2006 (Abstract).

Schierl, R. et al., Guidance Values for Surface Monitoring of Antineoplastic Drugs in German Pharmacies, *Am. Occup. Hyg.*, 53(7): 703-11, 2009, Online Jul. 20, 2009.

Sorsa, M. et al., Monitoring of occupational exposure to cytostatic anticancer agents, *Mutat. Res.*, 355(1-2): 253-61, Aug. 17, 1996 (Abstract).

Turci, R. et al., Biological and environmental monitoring of hospital personnel exposed to antineoplastic agents: a review of analytical methods, *Journal of Chromatography B*, 789: 169-209, 2003.

Yoshida, J. et al., Association between occupational exposure levels of antineoplastic drugs and work environment in five hospitals in Japan, *Journal of Oncology Pharmacy Practice*, 17(1): 29-38, 2011, Online Aug. 10, 2010.

(Author Unknown) The Pharmaceutical Online Magazine, Novel Monoclonal Antibodies to Measure Levels of 5-Fluorouracil in Plasma, Jun. 6, 2006.

* cited by examiner

DIRECT READING DETECTION KITS FOR SURFACE CONTAMINATION BY ANTINEOPLASTIC DRUGS

REFERENCE TO RELATED APPLICATION

This application claims priority from U.S. Provisional Patent Application Ser. No. 61/672,059, filed Jul. 16, 2012, the entire content of which is incorporated herein by reference.

FIELD OF THE INVENTION

The present invention relates generally to methods, devices and kits to assay antineoplastic drugs in environmental samples. According to specific aspects, the present invention relates to methods, devices and kits for lateral flow assay of samples collected to detect or quantitate antineoplastic drug contamination of a work site surface.

BACKGROUND OF THE INVENTION

Antineoplastic drugs are used in the treatment of cancer and are themselves carcinogenic, mutagenic and teratogenic. Over eight million healthcare workers in the U.S. are potentially exposed during preparation, handling and administration of these drugs. Although NIOSH and OSHA guidelines for handling antineoplastic drugs are in place, studies continue to report worker exposure to these drugs. Recent reports have observed external contamination of drug vials and contamination on work site surfaces. Cleaning of contaminated areas is difficult and complicated by the lack of quick, inexpensive methods to determine the success of the cleanup. Although analytical methods are available for measuring antineoplastic drugs in environmental samples, these methods are complicated and time consuming, requiring shipment to outside labs, delaying the receipt of sampling results. In addition, these analytical methods require considerable expertise and can be expensive to employ on a routine basis.

There is a continuing need for methods, devices and kits to assay antineoplastic drugs in environmental samples, such as work site surfaces.

SUMMARY OF THE INVENTION

Methods of detecting antineoplastic drug contamination of a surface are provided by the present invention which include: providing a wetting solution compatible with the antineoplastic drug and formulated to promote release of the drug from the surface to be assayed; providing a solid matrix for reversible absorption of the antineoplastic drug; contacting the solid matrix with the wetting solution, generating an assay matrix; contacting the assay matrix and the surface, generating a surface sample; contacting the surface sample with a volume of wetting solution, generating a fluid test sample; assaying the antineoplastic drug in the fluid test sample by lateral flow assay to produce a detectable assay result; and detecting the detectable assay result, thereby detecting antineoplastic drug contamination of the surface.

Methods of detecting antineoplastic drug contamination of a surface are provided by the present invention which include: providing a wetting solution compatible with the antineoplastic drug and formulated to promote release of the drug from the surface to be assayed; providing a solid matrix for reversible absorption of the antineoplastic drug; contacting the solid matrix with the wetting solution, generating an assay matrix; contacting the assay matrix and the surface, generating a surface sample; contacting the surface sample with a volume of wetting solution, generating a fluid test sample; assaying the antineoplastic drug in the fluid test sample by lateral flow assay to produce a detectable assay result; detecting the detectable assay result, thereby detecting antineoplastic drug contamination of the surface; and comparing the assay result to a standard.

Non-limiting examples of antineoplastic drugs assayed according to methods of the present invention include, but are not limited to, doxorubicin, paclitaxel and 5-fluorouracil.

According to aspects of methods of the present invention, lateral flow assay includes: providing a lateral flow assay device, the device comprising a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the test detection zone comprises a non-diffusibly bound detection reagent and the control zone comprises a non-diffusibly bound control reagent, the solid or semi-solid porous support adjacent a wicking pad that promotes the capillary flow of the fluid test sample along a flow path including the conjugate pad and the solid or semi-solid porous support.

According to aspects of methods of the present invention, lateral flow assay includes: providing a lateral flow assay device, the device comprising a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the antineoplastic drug binding agent is an anti-antineoplastic drug antibody, and wherein the test detection zone comprises a non-diffusibly bound detection reagent and the control zone comprises a non-diffusibly bound control reagent, the solid or semi-solid porous support adjacent a wicking pad that promotes the capillary flow of the fluid test sample along a flow path including the conjugate pad and the solid or semi-solid porous support.

According to aspects of methods of the present invention, lateral flow assay includes: providing a lateral flow assay device, the device comprising a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the antineoplastic drug binding agent is an anti-antineoplastic drug antibody, and wherein the test detection zone comprises a non-diffusibly bound detection reagent, wherein the detection reagent is the neoplastic drug, and the control zone comprises a non-diffusibly bound control reagent, the solid or semi-solid porous support adjacent a wicking pad that promotes the capillary flow of the fluid test sample along a flow path including the conjugate pad and the solid or semi-solid porous support.

According to aspects of the present invention, the control reagent binds specifically to the anti-antineoplastic drug antibody. Optionally, the control reagent is an antibody which binds specifically to the anti-antineoplastic drug antibody.

Detecting the assay result is achieved by visual observation or electronic reader according to methods described herein.

According to aspects of the present invention, the wetting solution comprises a biologically compatible buffer, 0.01-10% v/v of a surfactant and/or 0.01-10% v/v of an organic solvent. Optionally, the organic solvent is an organic polar protic solvent. Optionally, the surfactant is a non-ionic surfactant.

Lateral flow assay devices for detecting an antineoplastic drug according to aspects of the present invention include a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the test detection zone comprises a non-diffusibly bound detection reagent and the control zone comprises a non-diffusibly bound control reagent, the solid or semi-solid porous support adjacent a wicking pad that promotes the capillary flow of the fluid test sample along a flow path including the conjugate pad and the solid or semi-solid porous support.

An included antineoplastic drug binding agent is an anti-antineoplastic drug antibody according to aspects of the present invention.

An included detection reagent is a quantity of the neoplastic drug according to aspects of the present invention.

An included control reagent binds specifically to the anti-antineoplastic drug antibody according to aspects of the present invention. For example, the control reagent is an antibody which binds specifically to the anti-antineoplastic drug antibody.

Optionally, a device according to aspects of the present invention is a fluid test sample suspected of containing an antineoplastic drug.

Optionally, a device according to aspects of the present invention further comprises a housing at least partially enclosing the conjugate pad, the solid or semi-solid porous support, and/or the wicking pad.

A fluid test sample which contains or is suspected of containing an antineoplastic drug is added to a sample pad disposed adjacent the conjugate pad such that the fluid test sample flows in the direction of the adjacent conjugate pad. The fluid test sample may also be directly deposited on the conjugate pad or a portion of the conjugate pad designated as the sample pad. A lateral flow assay device according to aspects of the present invention includes a sample pad disposed adjacent the conjugate pad such that the fluid test sample flows in the direction of the adjacent conjugate pad.

A lateral flow assay device for detecting an antineoplastic drug according to aspects of the present invention includes a sample pad adjacent a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the test detection zone comprises a non-diffusibly bound detection reagent and the control zone comprises a non-diffusibly bound control reagent, the solid or semi-solid porous support adjacent a wicking pad that promotes the capillary flow of the fluid test sample along a flow path including the sample pad, the conjugate pad and the solid or semi-solid porous support.

Kits for detecting antineoplastic drug contamination of a surface, are provided according to aspects of the present invention which include a wetting solution compatible with the antineoplastic drug and formulated to promote release of the drug from the surface to be assayed; a solid matrix for reversible absorption of the antineoplastic drug; and a lateral flow device comprising: a binding agent specific for the antineoplastic drug; and a control reagent.

A lateral flow assay device included in an inventive kit according to aspects of the present invention includes a conjugate pad, a solid or semi-solid porous support adjacent the conjugate pad, a test zone present on the support and a control zone present on the support, wherein the binding agent is a detectably labeled antineoplastic drug binding agent diffusibly bound to a conjugate pad, wherein the test detection zone comprises a non-diffusibly bound detection reagent and the control reagent is non-diffusibly bound to a control zone, the solid or semi-solid porous support adjacent a wicking pad that promotes the capillary flow of the fluid test sample along a flow path including the conjugate pad and the solid or semi-solid porous support.

A lateral flow assay device included in an inventive kit according to aspects of the present invention includes a sample pad adjacent a conjugate pad, a solid or semi-solid porous support adjacent the conjugate pad, a test zone present on the support and a control zone present on the support, wherein the conjugate pad comprises a diffusibly bound detectably labeled antineoplastic drug binding agent, wherein the test detection zone comprises a non-diffusibly bound detection reagent and the control zone comprises a non-diffusibly bound control reagent, the solid or semi-solid porous support adjacent a wicking pad that promotes the capillary flow of the fluid test sample along a flow path including the sample pad, the conjugate pad and the solid or semi-solid porous support.

An included antineoplastic drug binding agent is an anti-antineoplastic drug antibody according to aspects of the present invention.

An included detection reagent is a quantity of the neoplastic drug according to aspects of the present invention.

An included control reagent binds specifically to the anti-antineoplastic drug antibody according to aspects of the present invention. For example, the control reagent is an antibody which binds specifically to the anti-antineoplastic drug antibody.

According to aspects of the present invention, the wetting solution included in an inventive kit comprises a biologically compatible buffer, 0.01-10% v/v of a surfactant and/or 0.01-10% v/v of an organic solvent. Optionally, an organic solvent included in an inventive kit is an organic polar protic solvent. Optionally, a surfactant included in an inventive kit is a non-ionic surfactant.

DETAILED DESCRIPTION OF THE INVENTION

Figure 1:
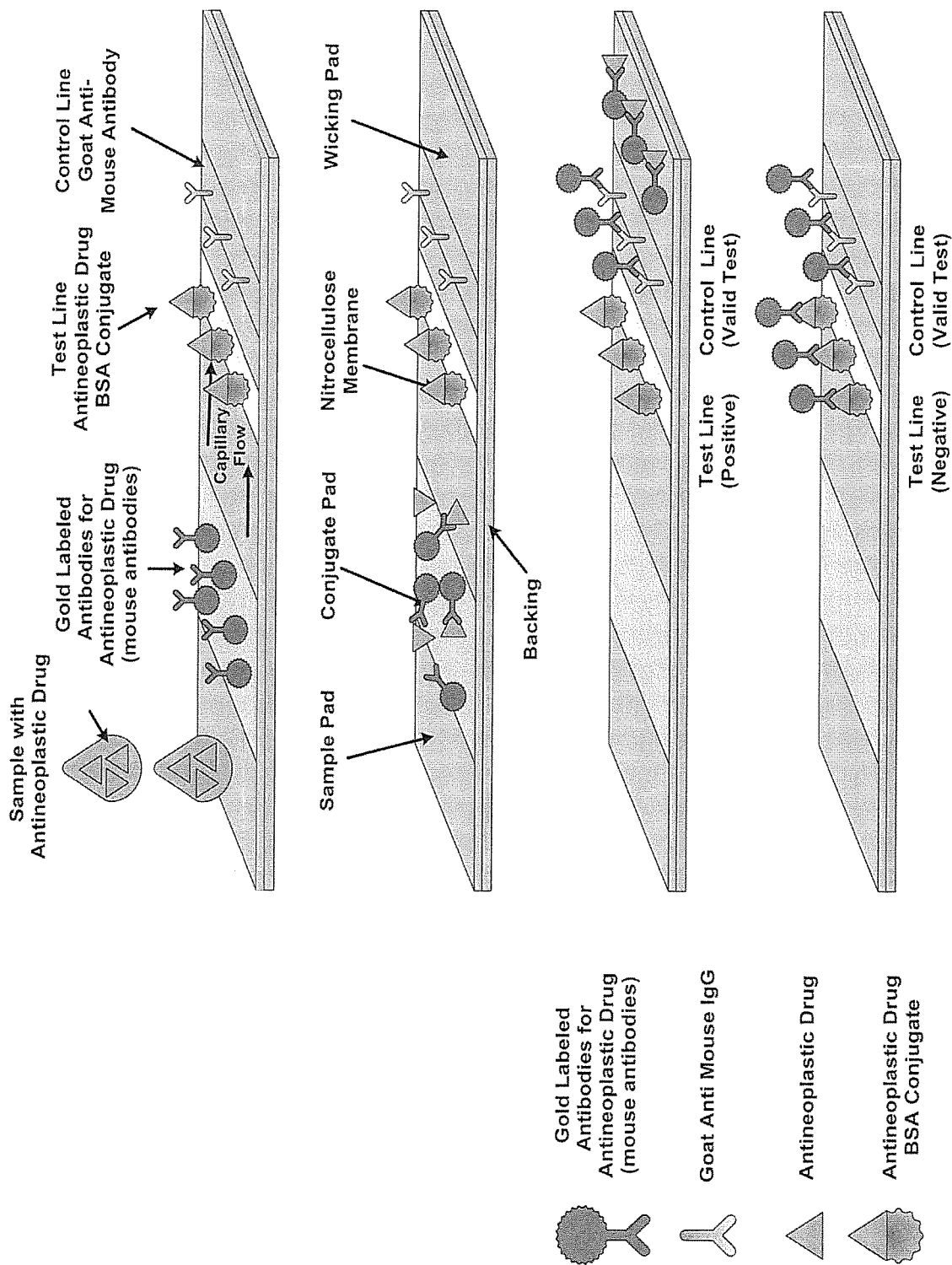
FIG. 1 is a schematic illustration of a device and method for lateral flow assay of an antineoplastic drug according to aspects of the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Wild, D., The Immunoassay Handbook, 3rd Ed., Elsevier Science, 2005; Gosling, J. P., Immunoassays: A Practical Approach, Practical Approach Series, Oxford University Press, 2005; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Ormerod, M. G., Flow Cytometry: a practical approach, Oxford University Press, 2000; Givan, A. L., Flow Cytometry: first principles, Wiley, New York, 2001; and Herdewijn, P. (Ed.), Oligonucleotide Synthesis: Methods and Applications, Methods in Molecular Biology, Humana Press, 2004.

The singular terms "a," "an," and "the" are not intended to be limiting and include plural referents unless explicitly state or the context clearly indicates otherwise.

Methods for detecting antineoplastic drug contamination of a surface are provided according to aspects of the present invention which include: providing a wetting solution compatible with the antineoplastic drug and formulated to promote release of the drug from the surface to be assayed; providing a solid matrix for reversible absorption of the antineoplastic drug; contacting the solid matrix with the wetting solution, generating an assay matrix; contacting the assay matrix and the surface, generating a surface sample; contacting the surface sample with a volume of wetting solution, generating a fluid test sample; and quantifying the antineoplastic drug in the fluid test sample by lateral flow assay to produce an assay result, thereby detecting antineoplastic drug contamination of the surface.

The assay result is compared to a standard according to preferred aspects of the invention.

A wetting solution compatible with the antineoplastic drug is substantially inert with respect to the drug.

A wetting solution includes a biologically compatible buffer and optionally includes a surfactant and/or a small amount of an organic solvent.

Examples of biologically compatible buffers include, but are not limited to, ammonium acetate, MOPS buffers, citrate buffers, HEPES buffers, carbonate buffers, Tris buffers, Tricine buffers, acetate buffers, phosphate buffers and phosphate buffered saline.

A surfactant is included in amounts of 0.01-10% v/v according to aspects of the present invention.

An included surfactant may be an anionic, cationic or nonionic surfactant.

Nonionic surfactants included in wetting solutions of the present invention are exemplified by, but not limited to, fatty acid esters and alkoxylated fatty alcohols. Nonionic surfactants included in wetting solutions of the present invention are exemplified by, but not limited to, glycerol alkyl esters, polyoxyethylene glycol alkyl ethers, polyoxypropylene glycol alkyl ethers, polyoxyethylene glycol octylphenol ethers, polyoxyethylene glycol alkylphenol ethers, polyoxyethylene glycol sorbitan alkyl esters, propoxylated polyoxyethylene ethers, poloxamers, polysorbates, sorbitan alkyl esters, and block copolymers of polyethylene glycol and polypropylene glycol. Nonionic surfactants included in wetting solutions of the present invention are exemplified by, but not limited to, Brij, cocamide MEA, cocamide DEA, decyl glucoside, dodecyldimethylamine oxide, glyceryl laurate, Nonoxynol-9, octaethylene glycol monododecyl ether; lauryl glucoside, octyl glucoside, pentaethylene glycol monododecyl ether, poloxamer 407, polysorbate 20, polysorbate 40, polysorbate 60, polysorbate 80, polyethoxylated tallow amine (POEA), Spans and Triton X-100.

Non-limiting examples of surfactants included according to aspects of the present invention are nonionic surfactants such as polysorbate 20, commercially available as Tween® 20.

According to aspects of the present invention a wetting solution includes a biologically compatible buffer and includes a surfactant and/or 0.01-10% v/v of an organic solvent.

A non-limiting example of a wetting solution is aqueous 10 mM ammonium acetate-1% Tween 20 (v/v).

According to aspects of the present invention a wetting solution includes a biologically compatible buffer and includes a surfactant and/or 0.01-10% v/v of an organic polar protic solvent. Organic polar protic solvents are well-known in the art and illustratively include, but are not limited to, methanol, propanol and ethanol.

The solid matrix used allows for reversible absorption of the antineoplastic drug to be assayed without substantial change to the chemical structure of the drug. Non-limiting examples of a solid matrix include filter papers, cotton matrices, foam matrices and cellulosic matrices, where such matrices are exemplified by, but not limited to, swabs, wipes and gauzes.

A sample is collected from one or more work site surfaces according to aspects of the present invention. Such work site surfaces are those present at sites of manufacture, packaging, testing, use and/or disposal of the antineoplastic drug. Non-limiting examples of work site surfaces from which a sample is collected, include bench tops, counters, desk surfaces, laboratory fume or isolation hoods, autoclaves, glassware, plasticware, clothing, floors, walls, ceilings, handles including door, drawer and cabinet handles, appliances and equipment surfaces.

Various antineoplastic drugs can be assayed using methods, devices and kits of the present invention, exemplified by doxorubicin, paclitaxel and 5-fluorouracil.

Antineoplastic drugs are described, for example, in Goodman et al., Goodman and Gilman's The Pharmacological Basis of Therapeutics, 8th Ed., Macmillan Publishing Co., 1990.

Antineoplastic drugs that can be assayed according to aspects of the present invention include, but are not limited to, acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, fluorocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

According to aspects of the present invention, immunoassay includes assay of an antineoplastic drug in a fluid test sample by an immunochromatography technique. Broadly described, immunochromatography techniques include flowing a fluid test sample containing or suspected of containing an analyte of interest along a solid or semi-solid support including an anti-analyte antibody to detect specific binding of the antibody and analyte.

According to aspects of the present invention, assay of an antineoplastic drug in a sample includes antigen capture, such as by lateral flow assay.

A lateral flow assay according to aspects of the present invention includes flowing a fluid test sample containing or suspected of containing an antineoplastic drug along a solid or semi-solid support including an anti-antineoplastic drug binding agent to detect specific binding of the anti-antineoplastic drug binding agent and the antineoplastic drug in the fluid test sample.

A lateral flow assay according to aspects of the present invention includes flowing a fluid test sample obtained along a solid or semi-solid support including an anti-antineoplastic drug binding agent, such as an antibody, in the presence of a competitor to detect competition for binding of the anti-antineoplastic drug binding agent, such as an antibody, with the antineoplastic drug in the fluid test sample.

According to aspects of the present invention, a lateral flow assay process for assay of an antineoplastic drug includes providing: a conjugate pad where detectably labeled anti-antineoplastic drug binding agent, such as an antibody, or detectably labeled antineoplastic drug is diffusibly bound, the conjugate pad adjacent a solid or semi-solid porous support which allows for lateral flow of the fluid test sample and which has at least one test detection zone including a non-diffusibly bound detection reagent and at least one control zone including a non-diffusibly bound control reagent, the solid or semi-solid porous support adjacent a wicking pad that promotes the capillary flow of the fluid test sample along a flow path including the conjugate pad and the solid or semi-solid porous support.

A non-diffusibly bound detection reagent is an anti-antineoplastic drug binding agent, such as an antibody. According to aspects of the present invention in which the conjugate pad contains a detectably labeled anti-antineoplastic drug binding agent, the detection reagent is non-competitive with the detectably labeled anti-antineoplastic drug binding agent.

A fluid test sample containing or suspect of containing an antineoplastic drug of interest is applied to the conjugate pad.

According to aspects where a detectably labeled antineoplastic drug binding agent is included in the conjugate pad, the detectable label is detected in the test zone to assay antineoplastic drug in the sample and greater amounts of detected detectable label are indicative of greater amounts of antineoplastic drug in the sample. According to aspects where a detectably labeled antineoplastic drug is included in the conjugate pad, the detectable label is detected in the test zone to assay antineoplastic drug in the fluid test sample and lower amounts of detected detectable label are indicative of greater amounts of antineoplastic drug in the fluid test sample.

One or more standards may be used to associate an amount of detected detectable label with an amount of antineoplastic drug in a sample.

The conjugate pad and/or support are optionally blocked to inhibit non-specific binding. Non-limiting examples of an optionally applied blocking reagent include a solution, optionally buffered, of non-fat dry milk, 1-5% bovine serum albumin, and further optionally including 0.1-0.3% detergent, such as Tween® 20 or TRITON-X 100. A further non-limiting example of a blocking reagent is 10 mM Borate, 3% BSA, 1%, PVP-40, 0.25% TRITON X-100, pH 8.

Any reaction or diluent buffer compatible with the sample, reagents and reaction can be used, including, but not limited to, phosphate buffered saline, ammonium acetate, sodium phosphate buffer, potassium phosphate buffer, Tris-HCl buffer and Tricine buffer.

The conjugate pad is disposed adjacent to the solid or semi-solid porous support and the solid or semi-solid porous support is disposed adjacent to the wicking pad. According to aspects of the inventive device, each component, the conjugate pad, the solid or semi-solid porous support and the wicking pad has a top surface in substantially the same plane as the top surface of each other component. The conjugate pad, the solid or semi-solid porous support and the wicking pad may be attached together so that they may be moved as one unit. Alternatively or additionally, the conjugate pad, the solid or semi-solid porous support and the wicking pad may all be attached to a structural support, such as a backing material for support and so that they may be moved as one unit.

A sample pad disposed adjacent the conjugate pad such that the fluid test sample flows in the direction of the adjacent conjugate pad may be included. According to aspects of the inventive device, each component, the sample pad, the conjugate pad, the solid or semi-solid porous support and the wicking pad has a top surface in substantially the same plane as the top surface of each other component. The sample pad, the conjugate pad, the solid or semi-solid porous support and the wicking pad may be attached together so that they may be moved as one unit. Alternatively or additionally, the sample pad, the conjugate pad, the solid or semi-solid porous support and the wicking pad may all be attached to a structural support, such as a backing material for support and so that they may be moved as one unit.

According to aspects of the present invention, a lateral flow assay method to detect an antineoplastic drug in a fluid test sample is competitive or non-competitive.

According to aspects of the present invention, a lateral flow assay device is provided including 1) a conjugate pad where detectably labeled anti-antineoplastic drug antibody or detectably labeled antineoplastic drug is diffusibly bound, 2) a solid or semi-solid porous support which allows for lateral flow of the fluid test sample and which has at least one test detection zone including a non-diffusibly bound detection reagent and at least one control zone including a non-diffusibly bound control reagent, and 3) a wicking pad that allows for the capillary flow of the fluid test sample.

According to aspects of the present invention, a lateral flow assay device is provided including 1) a conjugate pad where detectably labeled anti-5-fluorouracil antibody or detectably labeled 5-fluorouracil is diffusibly bound, 2) a solid or semi-solid porous support which allows for lateral flow of the fluid test sample and which has at least one test detection zone including a non-diffusibly bound detection reagent and at least one control zone including a non-diffusibly bound control reagent, and 3) a wicking pad that allows for the capillary flow of the fluid test sample.

According to aspects of the present invention, a lateral flow assay device is provided including 1) a conjugate pad where detectably labeled anti-paclitaxel antibody or detectably labeled paclitaxel is diffusibly bound, 2) a solid or semi-solid porous support which allows for lateral flow of the fluid test sample and which has at least one test detection zone including a non-diffusibly bound detection reagent and at least one control zone including a non-diffusibly bound control reagent, and 3) a wicking pad that allows for the capillary flow of the fluid test sample.

According to aspects of the present invention, a lateral flow assay device is provided including 1) a conjugate pad where detectably labeled anti-doxorubicin antibody or detectably labeled doxorubicin is diffusibly bound, 2) a solid or semi-solid porous support which allows for lateral flow of the fluid test sample and which has at least one test detection zone including a non-diffusibly bound detection reagent and at least one control zone including a non-diffusibly bound control reagent, and 3) a wicking pad that allows for the capillary flow of the fluid test sample.

FIG. 1 is a schematic illustration of a device and method for lateral flow assay of an antineoplastic drug according to aspects of the present invention. The conjugate pad, solid or semi-solid porous support (here indicated as nitrocellulose membrane) and wicking pad are attached and disposed adjacent to one another. The conjugate pad, solid or semi-solid porous support, and wicking pad each have at least a top surface substantially the same plane as each other top surface. The direction of lateral flow is shown. A test zone and a control zone are shown.

According to aspects of the present invention, a competitive lateral flow assay includes aspects shown in FIG. 1. A first detectably labeled binding agent capable of specific binding to an antineoplastic drug (here exemplified by "gold labeled antibodies for antineoplastic drug") is diffusibly attached to the conjugate pad. A fluid test sample which contains or is suspected of containing an antineoplastic drug is added to a sample pad disposed adjacent the conjugate pad such that the fluid test sample flows in the direction of the adjacent conjugate pad. The fluid test sample may also be directly deposited on the conjugate pad or a portion of the conjugate pad designated as the sample pad. The antineoplastic drug and first detectably labeled binding agent capable of specific binding to the antineoplastic drug form a complex at the conjugate pad. The complex, along with any unbound first detectably labeled binding agent is moved by lateral flow in the direction of the test zone and control zone. The test zone contains antineoplastic drug non-diffusibly affixed to the test zone. The control zone contains a second binding agent specific for the first detectably labeled binding agent. Excess first detectably labeled binding agent capable of specific binding to the antineoplastic drug moves by lateral flow to the test and control zones. If excess first detectably labeled binding agent binds to the antineoplastic drug in the test zone, a detectable signal is present indicative which varies directly with the amount of the antineoplastic drug in the fluid test sample, where strongly detectable signal is indicative of little or no antineoplastic drug in the sample and where undetectable signal in the test zone is indicative of the presence of the antineoplastic drug in the fluid test sample. Standards may be used to obtain quantitative or semi-quantitative results indicative of the amount of the antineoplastic drug in the sample. Interaction of the first detectably labeled binding agent with the second binding agent specific for the first detectably labeled binding agent produces a detectable signal indicative of a properly working assay.

In the example shown in FIG. 1, the first detectably labeled binding agent is an antibody generated in mouse and the second binding agent specific for the first detectably labeled binding agent is goat anti-mouse IgG. Where the first detectably labeled binding agent is an IgG (or other) antibody generated in mouse, the second binding agent may be an anti-mouse IgG (or other) antibody in any suitable species to generate, for example, sheep anti-mouse, rabbit anti-mouse or mouse anti-mouse. Similarly, if the first detectably labeled binding agent is an IgG (or other) antibody generated in rabbit, the second binding agent may be an anti-rabbit IgG (or other) antibody in any suitable species to generate, for example, sheep anti-rabbit, goat anti-rabbit or mouse anti-rabbit.

According to aspects, a lateral flow assay device, also called a monitor, of the present invention employs competitive lateral flow immunoassay to detect the presence of antineoplastic drugs on surfaces. A lateral flow assay monitor device according to aspects of the present invention includes: 1) an antibody specific for the antineoplastic drug to be assayed, the antibody conjugated to gold particles in the conjugate pad and 2) a predetermined amount of the same antineoplastic drug conjugated to BSA is present at the test line. If there is anti-neoplastic drug in the sample applied to the sample pad, it will bind to the gold-particle conjugated antibodies specific for the drug and thereby decrease the binding of these antibodies to the drug BSA conjugate on the test line. Thus, a greater amount of antineoplastic drug present in the fluid test sample applied to the sample pad results in fewer gold particles binding to the test line compared to a fluid test sample containing a smaller amount of the antineoplastic drug. Since the gold particles impart a red color to the test line, the intensity of the red color at the test line is indicative of the amount of the antineoplastic drug in a sample, less color indicating more drug. A control line is also included according to aspects of a lateral flow assay monitor device and method of the present invention. The control line employs a different antibody interaction than the test line and provides a positive control for the lateral flow assay, ensuring that the lateral flow assay monitor device is performing properly. Competitive assay-drug in solution binds to gold labeled antibodies resulting in less antibody binding to drug-BSA conjugate at test line. In this example, the test line becomes less intense with increasing drug amount in the fluid test sample while control line is relatively constant, indicating that the lateral flow assay monitor device is working.

The term "diffusibly bound" refers to reversible attachment or adsorption of a material to the conjugate pad such that the material moves with the lateral flow when contacted with the biological sample. The term "non-diffusibly bound" refers to attachment of a material to the solid support wherein a non-diffusibly bound material is immobilized and therefore does not move with the lateral flow when contacted with the fluid test sample.

The term "test detection zone" refers to a region of the solid or semi-solid porous support where a detection reagent is non-diffusibly bound. The test detection zone may have any of various shapes and sizes configured to allow for determination of binding of an analyte to the detection reagent. Typically, the test detection zone is a line of non-diffusibly bound detection reagent, referred to as a "test line."

The term "control zone" refers to a region of the solid or semi-solid porous support where a control reagent is non-diffusibly bound. The control zone may have any of various shapes and sizes configured to allow for determination of binding of a control substance to the control reagent. Typically, the control zone is a line of non-diffusibly bound control reagent, referred to as a "control line."

A control reagent allows a user to confirm that the immunoassay is working properly. For example, a control reagent may be an antibody which specifically binds to the detectably labeled anti-antineoplastic drug antibody.

As noted above, according to aspects of the present invention, the test zone contains antineoplastic drug non-diffusibly bound to the test zone. The antineoplastic drug is optionally directly affixed to the solid or semi-solid porous support at a desired location. In a further option, the antineoplastic drug is conjugated to a carrier to aid in binding the antineoplastic drug to the support at a desired location and the carrier-antineoplastic drug conjugate is bound to the solid or semi-solid porous support. Suitable carriers are molecules capable of adsorption or covalent bonding to the support, including, but not limited to, polypeptides such as bovine serum albumin (BSA), lactalbumin, polylysine and keyhole limpet hemocyanin.

According to aspects of the present invention, a lateral flow assay device includes 1) detectably labeled anti-antineoplastic drug antibody diffusibly bound to the conjugate pad, 2) a solid or semi-solid porous support having a test detection zone including non-diffusibly bound second anti-antineoplastic drug antibody and 3) a wicking pad. According to this aspect, the detectably labeled anti-antineoplastic drug antibody diffusibly bound to the conjugate pad and the second anti-antineoplastic drug antibody non-diffusibly bound to the solid or semi-solid porous support bind specifically to different epitopes of the antineoplastic drug.

According to aspects of the present invention, a lateral flow assay device includes 1) a detectably labeled antineoplastic drug epitope diffusibly bound to the conjugate pad, 2) a solid or semi-solid porous support having a test detection zone including non-diffusibly bound anti-antineoplastic drug antibody and 3) a wicking pad. According to this aspect, the detectably labeled antineoplastic drug epitope diffusibly bound to the conjugate pad binds specifically to the anti-antineoplastic drug antibody non-diffusibly bound to the solid or semi-solid porous support and therefore competes with antineoplastic drug in a fluid test sample.

The sample pad is a material which facilitates lateral flow of the fluid test sample to the adjacent conjugate pad and which does not interfere with lateral flow of the antineoplastic drug to be assayed including, but not limited to, glass fiber, bound glass fiber, polyester, cellulose and cellulose derivatives include cellulose acetate and nitrocellulose, nylon, polyvinylidene fluoride, polyethylene, polycarbonate, polypropylene, polyethersulfone and combinations of any of these.

The conjugate pad is a material to which a detectably labeled antineoplastic drug binding agent may be diffusibly attached including, but not limited to, glass fiber, bound glass fiber, polyester, cellulose and cellulose derivatives include cellulose acetate and nitrocellulose, nylon, polyvinylidene fluoride, polyethylene, polycarbonate, polypropylene, polyethersulfone and combinations of any of these.

The a solid or semi-solid porous support may be any solid or semi-solid adsorbent porous material suitable for chromatographic applications including, but not limited to, polyvinylidene fluoride, nylon, polyether sulfone, polyester, polypropylene, paper, silica, rayon, cellulose and cellulose derivatives include cellulose acetate and nitrocellulose, woven or non-woven natural or synthetic fibers and porous gels such as agarose, gelatin, dextran and silica gel. The solid or semi-solid porous support may be self-supporting, such as a membrane, or may be deposited on a structural support, such as an agarose thin layer deposited on a glass slide. According to aspects of the invention, the solid or semi-solid porous support is a nitrocellulose membrane.

The wicking pad is an absorbent material that facilitates lateral flow by wicking fluid including, but not limited to, an absorbent synthetic or natural polymer, such as cellulose.

A structural support to which the sample pad, conjugate pad, solid or semi-solid porous support, and/or wicking pad are attached can be any material which provides support including, but not limited to, a backing card, glass, silica, ceramic and/or plastic membrane. An adhesive may be used to attach the conjugate pad, solid or semi-solid porous support, and/or wicking pad to the structural support.

A housing is optionally included to at least partially enclose the sample pad, the conjugate pad, solid or semi-solid porous support, and wicking pad. The housing optionally defines one or more openings such as for application of a sample to be assayed for an antineoplastic drug, visualization or other analysis of test and/or control results. The housing defines an opening for insertion and removal of the sample pad, the conjugate pad, solid or semi-solid porous support, and wicking pad.

The housing optionally defines openings to allow the user to directly visualize assay results. Alternatively, the housing may include a detection device, such as an optical scanner, for detection of assay results.

Detecting an assay result may be accomplished by visual observation and/or use of a detection device, such as, an electronic reader. An electronic reader used to detect results of a lateral flow assay is configured to detect the detectable label or labels used in the assay. Thus, for example, where the detectable label is gold particles, such as colloidal gold, or colored latex particles, a charged couple device (CCD) camera may be used to detect the signal of the detectable label. In a further example, where the detectable label is fluorescent, a suitable excitation source and sensor of the resulting emitted signal may be used. An electronic reader may generate data for analysis using one or more computer implemented methods. The electronic reader may include hardware and software components for computer implemented methods to analyze detected lateral flow assay results.

The fluid test sample flows by capillary action to a control line and a test line that have binding agents, preferably antibodies, disposed at a precise concentration determined through validation experiments. The control line is an internal quality control that ensures the sample has migrated appropriately and validates the assay. The test line determines a positive or negative result for the analyte tested.

Binding assays include use of a binding agent to detect an analyte.

The term "binding agent" as used herein refers to an agent characterized by substantially specific binding to a specified substance. The phrase "substantially specific binding" and grammatical equivalents as used herein in reference to binding of a binding agent to a specified substance refers to binding of the binding agent to the specified substance without substantial binding to other substances present in a sample to be assayed for presence of the specified substance. It is understood by the ordinarily skilled artisan that specific binding refers to specific binding as determinable by use of appropriate controls to distinguish it from nonspecific binding.

Binding agents substantially specific for antineoplastic drugs may be obtained from commercial sources or generated for use in methods of the present invention according to well-known methodologies.

The term "binding" refers to a physical or chemical interaction between a binding agent and the target. Binding includes, but is not limited to, ionic bonding, non-ionic bonding, covalent bonding, hydrogen bonding, hydrophobic interaction, hydrophilic interaction, and Van der Waals interaction.

Assaying an antineoplastic drug in a fluid test sample according to aspects of the present invention may include detection of a detectable label directly or indirectly attached to the antineoplastic drug. The term "detectable label" refers to any atom or moiety that can provide a detectable signal and which can be attached to a binding agent or analyte. Examples of such detectable labels include fluorescent moieties, chemiluminescent moieties, bioluminescent moieties, ligands, particles, magnetic particles, fluorescent particles, colloidal gold, enzymes, enzyme substrates, radioisotopes and chromophores. Methods for directly or indirectly attaching a detectable label to an antineoplastic drug are well-known in the art.

Any appropriate method, including but not limited to spectroscopic, optical, photochemical, biochemical, enzymatic, electrical and/or immunochemical is used to detect a detectable label in an assay described herein.

Compositions and methods are provided according to aspects of the present invention wherein a binding agent is an anti-antineoplastic drug antibody characterized by substantially specific binding for the antineoplastic drug. Compositions and methods are provided according to aspects of the present invention wherein a binding agent is an anti-5-fluorouracil antibody characterized by substantially specific binding for 5-fluorouracil (5-FU or FU). Compositions and methods are provided according to aspects of the present invention wherein a binding agent is an anti-paclitaxel antibody characterized by substantially specific binding for paclitaxel. Compositions and methods are provided according to aspects of the present invention wherein a binding agent is an anti-doxorubicin antibody characterized by substantially specific binding for doxorubicin.

The term "antibody" is used herein in its broadest sense and includes single antibodies and mixtures of antibodies characterized by substantially specific binding to an antigen. An antibody provided according to compositions and methods is illustratively a polyclonal antibody, a monoclonal antibody, a chimeric antibody, a humanized antibody, and/or an antigen binding antibody fragment, for example. The term antibody refers to a standard intact immunoglobulin having four polypeptide chains including two heavy chains (H) and two light chains (L) linked by disulfide bonds in particular embodiments. Antigen binding antibody fragments illustratively include an Fab fragment, an Fab' fragment, an F(ab')2 fragment, an Fd fragment, an Fv fragment, an scFv fragment and a domain antibody (dAb), for example. In addition, the term antibody refers to antibodies of various classes including IgG, IgM, IgA, IgD and IgE, as well as subclasses, illustratively including for example human subclasses IgG1, IgG2, IgG3 and IgG4 and murine subclasses IgG1, IgG2, IgG2a. IgG2b, IgG3 and IgGM, for example.

In particular embodiments, an antibody which is characterized by substantially specific binding has a dissociation constant, Kd, less than about $10^{-7}$ M, such as less than about $10^{-8}$ M, less than about $10^{-9}$ M or less than about $10^{-10}$ M, or less depending on the specific composition. Binding affinity of an antibody can be determined by Scatchard analysis such as described in P. J. Munson and D. Rodbard, Anal. Biochem., 107:220-239, 1980 or by other methods such as Biomolecular Interaction Analysis using plasmon resonance.

Antibodies and methods for preparation of antibodies are well-known in the art.

Broadly, an immunogen, such as a protein, peptide, antineoplastic drug, or immunogenic portion thereof, is administered to an animal in particular methods, such as a rabbit, goat, mouse, rat, sheep or chicken and immunoglobulins produced in the animal are obtained from the animal, and optionally, purified for screening and use.

An immunogen, such as a protein, peptide, antineoplastic drug, or immunogenic portions thereof, used to generate antibodies specific for the immunogen may be conjugated to a carrier, such as keyhole limpet hemocyanin or bovine serum albumin.

Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

Monoclonal antibodies may be used in assays according to aspects of the present invention. Monoclonal antibodies are prepared using techniques known in the art such as described in E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003, for example. Monoclonal antibodies according to the present invention and/or used in methods according to the present invention are produced by techniques illustratively including, but not limited to, hybridoma techniques, recombinant nucleic acid methodology and/or isolation from a phage library, for example as described in the above cited references. Monoclonal antibodies are advantageously used in particular embodiments due to the specificity of the binding of monoclonal antibodies which recognize a single epitope.

Particular methods of monoclonal antibody preparation include obtaining spleen cells from an animal immunized with an immunogen and fusing the antibody-secreting lymphocytes with myeloma or transformed cells to obtain a hybridoma cell capable of replicating indefinitely in culture.

Antibodies obtained are tested for substantially specific binding to the immunogen by methods illustratively including ELISA, Western blot and immunocytochemistry.

Aspects of inventive devices, kits and methods are illustrated in examples herein. These examples are provided for illustrative purposes and are not considered limitations on the scope of inventive devices, kits and methods.

EXAMPLES

Reagents and Monitor

The antibodies and drug-BSA conjugates used in this example were developed by Saladax Biomedical (Bethlehem, Pa.) and were purchased from Saladax Biomedical and Lampire Biological Laboratories (Pipersville, Pa.). Cotton swabs were Puritan model 806-WC (Puritan, Guilford, Me.). 5-fluorouracil (5-FU≥99%, product number F6627-1G) and Polyoxyethylenesorbitan monolaurate (Tween 20, product number P-1379) were purchased from Sigma-Aldrich (St. Louis, Mo.). Concentrated ammonium hydroxide (product A669-500) was from Fisher Scientific (Fair Lawn, N.J.).

5-FU Solution Preparation

The stock solution of 5-FU was prepared by dissolving a weighed amount of 5-FU between 10 and 25 mg in 1 ml of concentrated ammonium hydroxide. The spiking solutions were prepared by diluting the stock solution in 10 mM ammonium acetate as required to produce desired concentrations of 5-FU. This allowed a range of 5-FU spike levels to be applied using identical spike volumes, so all tiles would dry equally before wiping. Similar stock solutions of paclitaxel or doxorubicin were prepared for use as spiked sampling buffer controls or for surface sampling tests.

Surface Sampling

The surface sampling procedure was developed to be convenient and rapid. Ceramic bathroom tiles, vinyl floor tiles, counter top composite tiles, stainless steel tiles, and glass tiles of 100 cm$^2$ area were spiked with 50 µl spiking solution to give 0, 5, 10, 25, 50 or 100 ng of 5-FU surface loading (three tiles at each level) and allowed to dry for 2 hours. Each 100 cm$^2$ surface was completely wiped with a cotton swab wetted in vial containing 1 mL of sampling buffer (aqueous 10 mM ammonium acetate-1% Tween 20 (v/v)) first in an up and down direction, then in a sideways direction, and finally repeating the up and down wiping direction. The swab is then returned to the vial containing sampling buffer, agitated vigorously for 2 min, and a 75 µl aliquot of the resulting extract is applied to the lateral flow drug monitor (two for each of the extracts).

The same procedure was followed for surface sampling tests using paclitaxel or doxorubicin.

Monitor Testing

The monitors were tested with samples produced by surface wiping spiked tile surfaces with cotton swabs and extracting the swabs as described in the last section. In addition, the monitors were tested with control samples prepared (1) by directly spiking sampling buffer with spiking solution and (2) by directly spiking swabs that were then extracted. The spiked buffer controls demonstrate performance of the monitors without recovery losses or interference artifacts from the swabs or wiped surfaces. The spiked swab controls allow the contribution of the wipe media to the method performance (e.g., incomplete extraction of 5-FU from swabs) to be isolated and assessed. For spiked buffer controls, 50 µl of the appropriate spiking solution was added to 950 µl sampling buffer to yield 0, 5, 10, 25, 50 or 100 ng/mL of 5-FU. A 75 µl aliquot of the resulting extract was applied to the lateral flow drug monitor. For spiked swab controls, cotton swabs were spiked directly with 50 µl of 5-FU spiking solutions (one per spike level) and extracted with 950 µl sampling buffer using the same procedure used for the swabs from the tile wipe studies. A 75 µl aliquot of the resulting extract was applied to the lateral flow drug monitor. One tile material was tested each day, and a fresh set of 5-FU spiking solutions was made up to prepare each new set of spiked tiles, spiked buffer controls for that day and spiked swab controls.

Three monitors were used with spiked sampling buffer solutions and spiked swab solutions. The response of the monitors was evaluated using an electronic lateral flow reader (Hamamatsu model 10066) which read the intensity of the test and control lines. A visual reading method was also used where the intensity of the test line was compared to the control line. If the control line was more intense than the test line then the mass was determined to be above the threshold. Thus the monitors were evaluated for semi-quantitative results using the reader and qualitative results using the visual line comparison. The response for electronic and visual reading was determined 5, 10 and 15 min after adding solution to the monitors.

The same procedure was followed for tests using paclitaxel or doxorubicin.

LC-MS/MS

The lateral flow monitor was developed using 10 mM phosphate buffered saline (PBS)-1% Tween 20 as sampling buffer. However, it was found that PBS-1% Tween was incompatible with use of a LC-MS/MS method and therefore 10 mM ammonium acetate-1% Tween 20 was used as sampling buffer. The 10 mM ammonium acetate-1% Tween 20 gave nearly equivalent results to the PBS-1% Tween with the lateral flow monitors and allowed the same solutions that were used in the lateral flow assay to be analyzed directly by LC-MS/MS. This was an advantage since it would be difficult to ensure that separate solutions for the lateral flow assay and LC-MS/MS analysis would be equivalent.

The LC-MS/MS method was developed to measure 5-FU directly in the 10 mM ammonium acetate-1% Tween 20 sampling buffer used for the lateral flow monitors.

The chromatographic conditions used allowed adequate separation of the 5-FU analyte from the Tween and other components.

The HPLC column used was Waters YMC-ODS-AQ, 2.0×250 mm, 5 µm, (Waters Part No. AQ12S052502WT, Waters Corp, Milford, Mass.) run at 30° C. The mobile phase flow rate was 0.280 mL/min with mobile phase components A and B (A—2 mM ammonium acetate, aqueous, B—Methanol). A gradient of these components was used as follows:

| | |
|---|---|
| Isocratic 95% A, 5% B | 0-4.5 min |
| Gradient to 5% A, 95% B | 4.5-5.5 min, linear ramp |
| Isocratic 5% A, 95% B | 5.5-11 min |
| Gradient to 95% A, 5% B | 11-12 min, linear ramp |
| Isocratic 95% A, 5% B (re-equilibration) | 12-17 min |

15 µL of sample was injected onto the column and the elution time of the 5-fluorouracil analyte was approximately 4.5 min with a total run time of 17 min including re-equilibration. The mass spectrometer (Micromass Quattro LC (Waters Corp)) was operated in the electrospray negative ion ionization mode and employed a triple quadrapole to perform multiple reaction monitoring for the following transitions:

5-fluorouracil (analyte): mass to charge (m/z) 129 to 42
5-fluorouracil-$^{15}N_2$ (Internal standard at 20 ng/mL level): m/z 131 to 43)

The transitions were measured with a dwell time of 200 ms for each transition. Electrospray capillary voltage was 500 V, cone voltage was 30 V and fragmentation collision energy was 14 eV for both transitions. The validated linear calibration range was 0-250 ng/mL 5-FU in sampling buffer which allowed all test samples to be analyzed without prior dilution. Limits of detection and quantification evaluated using a regression plot generated from low level 5FU standards prepared in sampling buffer were 0.30 and 0.84 ng/mL, equivalent to 0.30 and 0.84 ng in 1 mL test samples.

The chromatographic conditions used allowed adequate separation of the 5-FU analyte from the Tween 20 and other components. The limit of detection (LOD) was 0.3 ng/mL and the limit of quantification (LOQ) was 0.84 ng/mL with a precision of 3% or better for spiked solutions over the demonstrated calibration linear dynamic range of 0-250 ng/mL. The LC-MS/MS was calibrated with standard solutions prepared in sampling buffer by the LC-MS/MS analyst from the contract laboratory Bureau Veritas North America (BVNA). LC-MS/MS analysis was done on solutions from spiked sampling buffer, spiked swabs, and spiked tiles at 0, 10, 25 and 100 ng.

Data Interpretation

As mentioned above the response of the monitors was evaluated with both the electronic reader and visual interpretation.

Electronic Reader

The line intensities from the electronic reader were treated in two ways. % B/Bo (where B is the test line intensity at given mass and Bo is the test line intensity at 0 mass) was calculated and plotted against spiked mass of 5-FU for spiked buffer controls, spiked swab controls, and spiked tile samples, or for paclitaxel and doxorubicin for spiked buffer controls and spiked tile samples. % B/Bo for all sample types was fitted against log of spiked mass to produce a calibration curve. The ratio of the Control line intensity to the Test line intensity (C/T ratio) was also calculated and plotted directly against spiked mass to also produce a second calibration curve. Assessment of the "goodness of fit" of the % B/Bo versus log mass and C/T versus mass curves was investigated by evaluating the fit of the standards data to the % B/Bo or C/T model by "standards recovery" (Nix and Wild, 2001), calculated by evaluating interpolated results from each fitted (observed) mass and comparing it to the mass of each antineoplastic drug spiked (expected mass). The recovered mass was calculated for the spiked swabs and spiked tiles by calculating the mass recovered at each calibration point using the fitted % B/Bo and C/T curves for the spiked sampling buffer controls and the % B/Bo and C/T response for the solutions from the spiked swab controls and spiked tile samples.

Visual Interpretation

The visual interpretation involved evaluation of whether the Control line (C) or the Test line (T) by visually determining which line was more intense. If the lines were judged as equal then (=) was used. If the lines were judged as close to equal but the test line was slightly brighter then (T=) was used and if control line was slightly brighter then (C=) was used.

LC-MS/MS Validation

For the LC-MS/MS validation, the masses measured via the LC-MS/MS method were correlated with the known spiked masses for spiked buffer control solutions, spiked swab controls, and tile samples. The recovered mass measured with the lateral flow monitors was also correlated with the mass measured via LC-MS/MS.

Lateral Flow Immunoassays

Note that all data presented are for 15 min after adding the solution to the monitors; data obtained at 5 min and 10 min after adding the solution to the monitors gives similar results for % B/Bo.

Spiked Sampling Buffer Control Samples

Figure 2A:
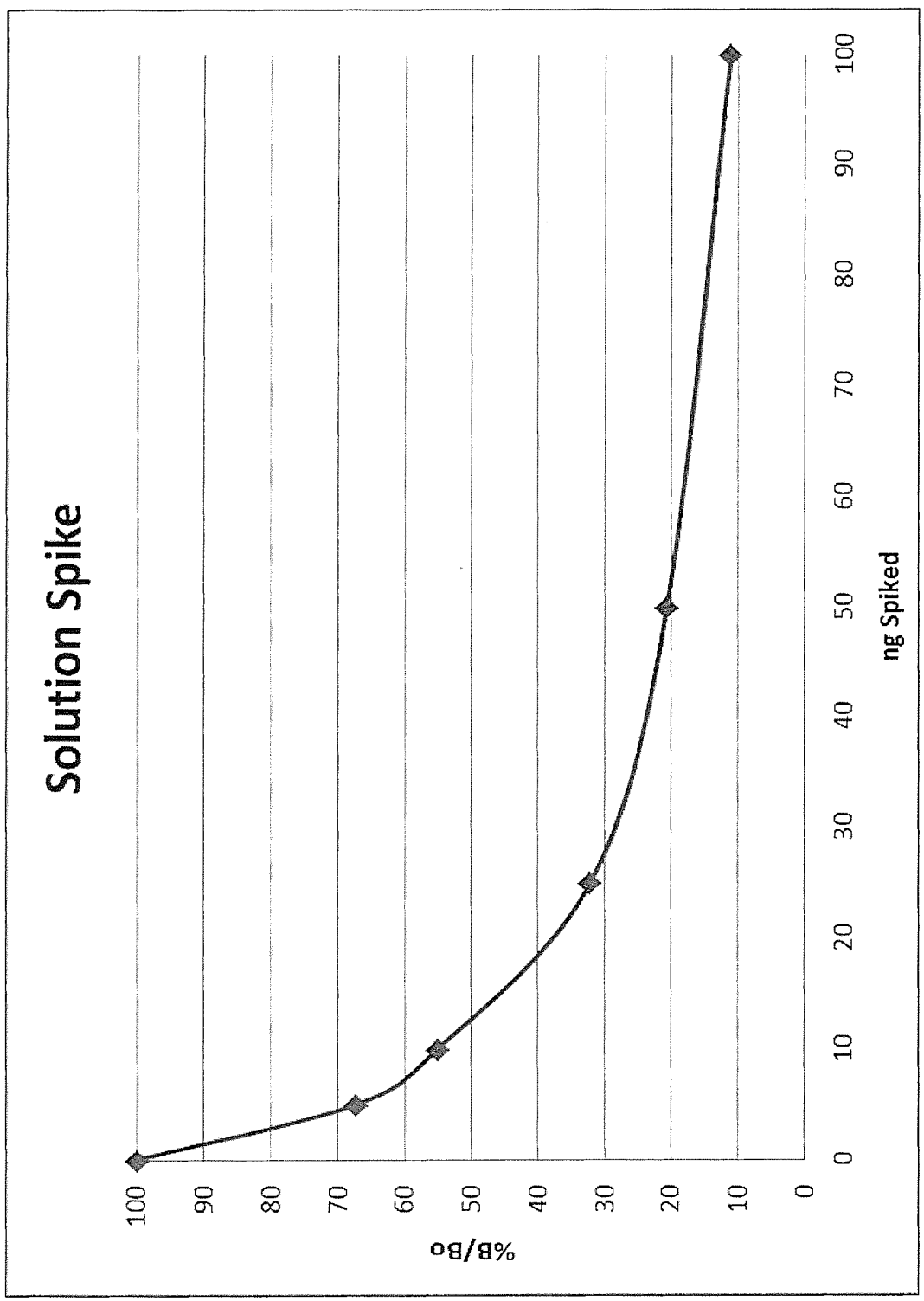
FIG. 2A is a graph showing lateral flow monitor response for spiked sampling buffer as % B/Bo.
Figure 2B:
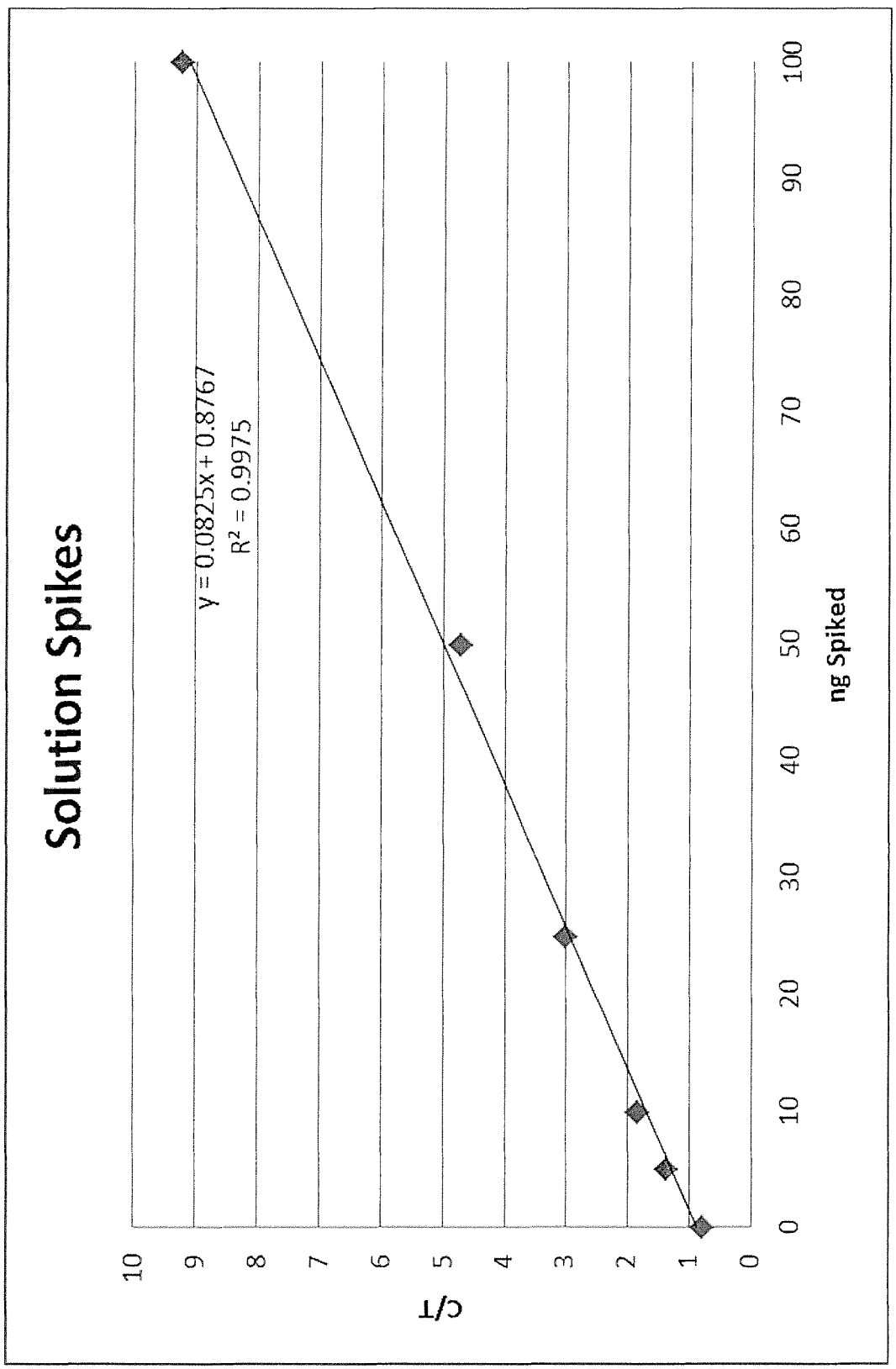
FIG. 2B is a graph showing lateral flow monitor response for spiked sampling buffer as C/T Ratio.

FIG. 2A is a graph showing lateral flow monitor response for spiked sampling buffer as % B/Bo. The sampling buffer was spiked with increasing masses of 5-FU and the response of the monitors was measured and presented as % B/Bo where B is the response at a given mass and Bo is the response at 0 mass. FIG. 2B is a graph showing lateral flow monitor response for spiked sampling buffer as C/T Ratio. Sampling buffer was spiked with increasing masses of 5-FU and the response of the monitors was measured and presented as C/T ratio where C is the control line intensity and T is the test line intensity.

The data shown in FIGS. 2A and 2B are the average for the five sets of spiked buffer control samples, each of which was prepared and analyzed to accompany one of the tile wipe studies done on five different surfaces. The % B/Bo shows an average % B/Bo of 67% at 5 ng 5-FU spiked with a CV of about 10% indicating that this amount is detectable when spiked directly into the sampling buffer. The C/T ratio was fitted with a straight line as a function of spiked mass which shows good correlation. % B/Bo was fitted against the log of concentration and this fit was used to back calculate observed mass at each of the points. Likewise the fitted C/T curve was used to back calculate observed mass.

Figure 2C:
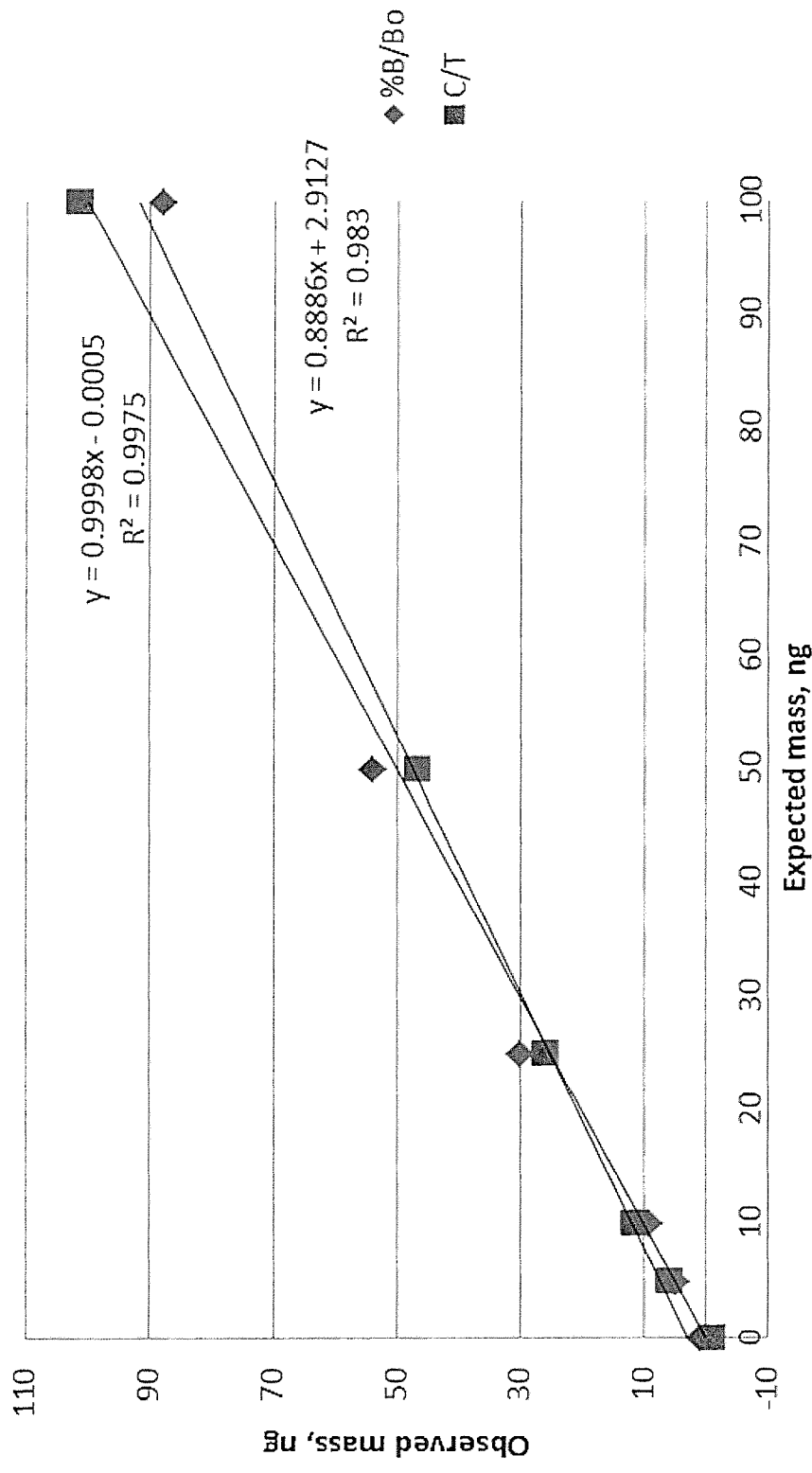
FIG. 2C is a graph showing the (observed mass) as a function of expected mass using % B/Bo and C/T curves indicating good fit for the data.

FIG. 2C is a graph showing the (observed mass) as a function of expected mass using % B/Bo and C/T curves indicating good fit for the data. The standards recovery was calculated by plotting the interpolated results from either % B/Bo versus log mass or C/T versus mass fitted curves (the observed mass) against the mass of 5-FU spiked in the buffer (the expected mass). The response curve can be modeled with % B/Bo versus log spiked mass or C/T versus spiked mass and both give good correlation of observed versus expected mass.

The good correlation (slope=1.01, intercept=−0.23, $R^2$=0.9999) of the LC-MS/MS measurement with spiked mass 5-FU for spiked buffer controls indicates that the spiking technique used to prepare in-house test samples for this investigation was accurate, see Table IIIA. It also indicates that although the calibration standards prepared for LC-MS analysis used a different 5FU supply than in-house samples, quantitative accuracy of prepared samples was reliable.

The C/T is easy to calculate and gives some compensation for variation in the lateral flow monitors since the test line and control line intensity tend to rise and fall together. The visual interpretation indicates that 5 ng spiked mass is detectable since all monitors give C= to C at this mass and all are C for 10 ng spike level. Table I shows the visual interpretation for the spiked buffer controls and the control line (C) was judged more intense than the test line (T) at 5-10 ng spiked level.

the response at 0 mass. FIG. 3B is a graph showing monitor response for solutions from spiked swabs as C/T Ratio. Swabs were spiked with increasing masses of 5-FU and the response of the monitors to solutions extracted from the swabs was measured and presented as C/T ratio where C is the control line intensity and T is the test line intensity.

These data shown are again the average for 5 sets of spiked swab data, each collected to accompany the tile wipe studies performed on different surfaces. % B/Bo show an average of 74% with CV of 20% at 10 ng spiked indicating this mass would be detectable from spiked swabs. The C/T and % B/Bo were fitted the same way as with the solutions and used to calculate observed mass. For the spiked swab controls, the average % B/Bo was 74% at 10 ng indicating that this mass of 5-FU can be detected. The response could be modeled with % B/Bo versus log mass or C/T versus mass and the observed versus expected mass gave good correlation with either fit, FIG. 3C.

Figure 3A:
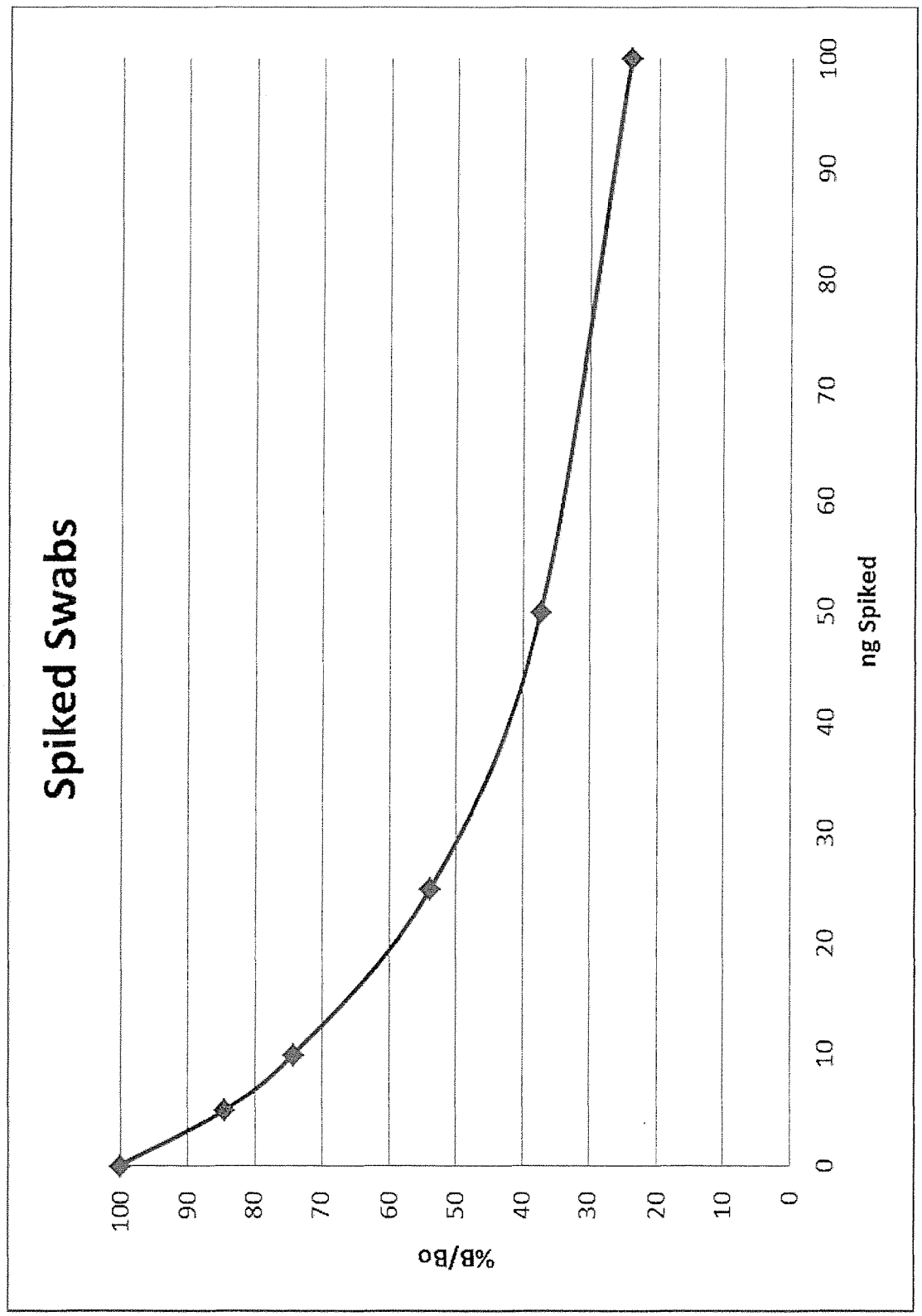
FIG. 3A is a graph showing monitor response for solutions from spiked swabs as % B/Bo.
Figure 3B:
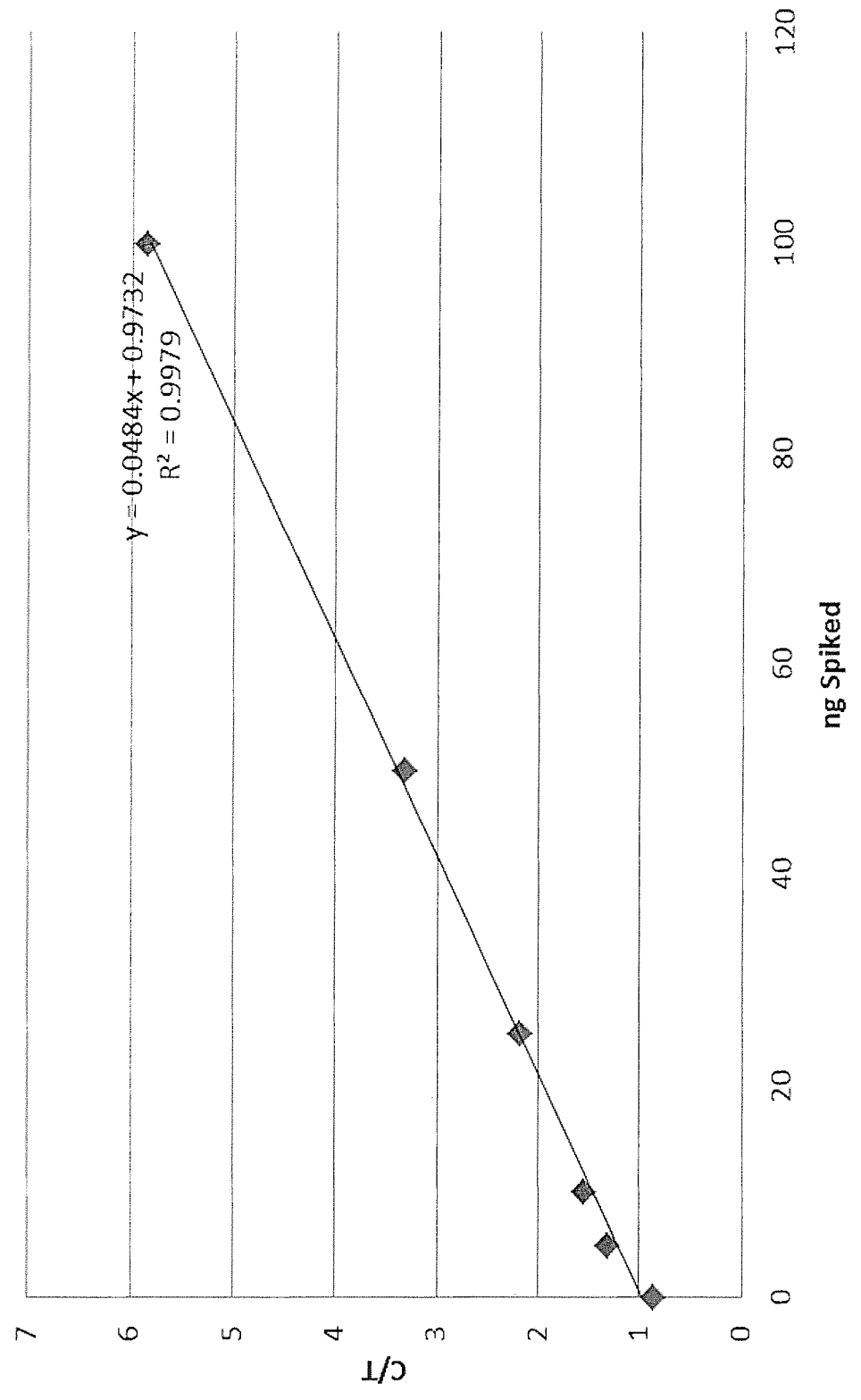
FIG. 3B is a graph showing monitor response for solutions from spiked swabs as Ca Ratio.
Figure 3C:
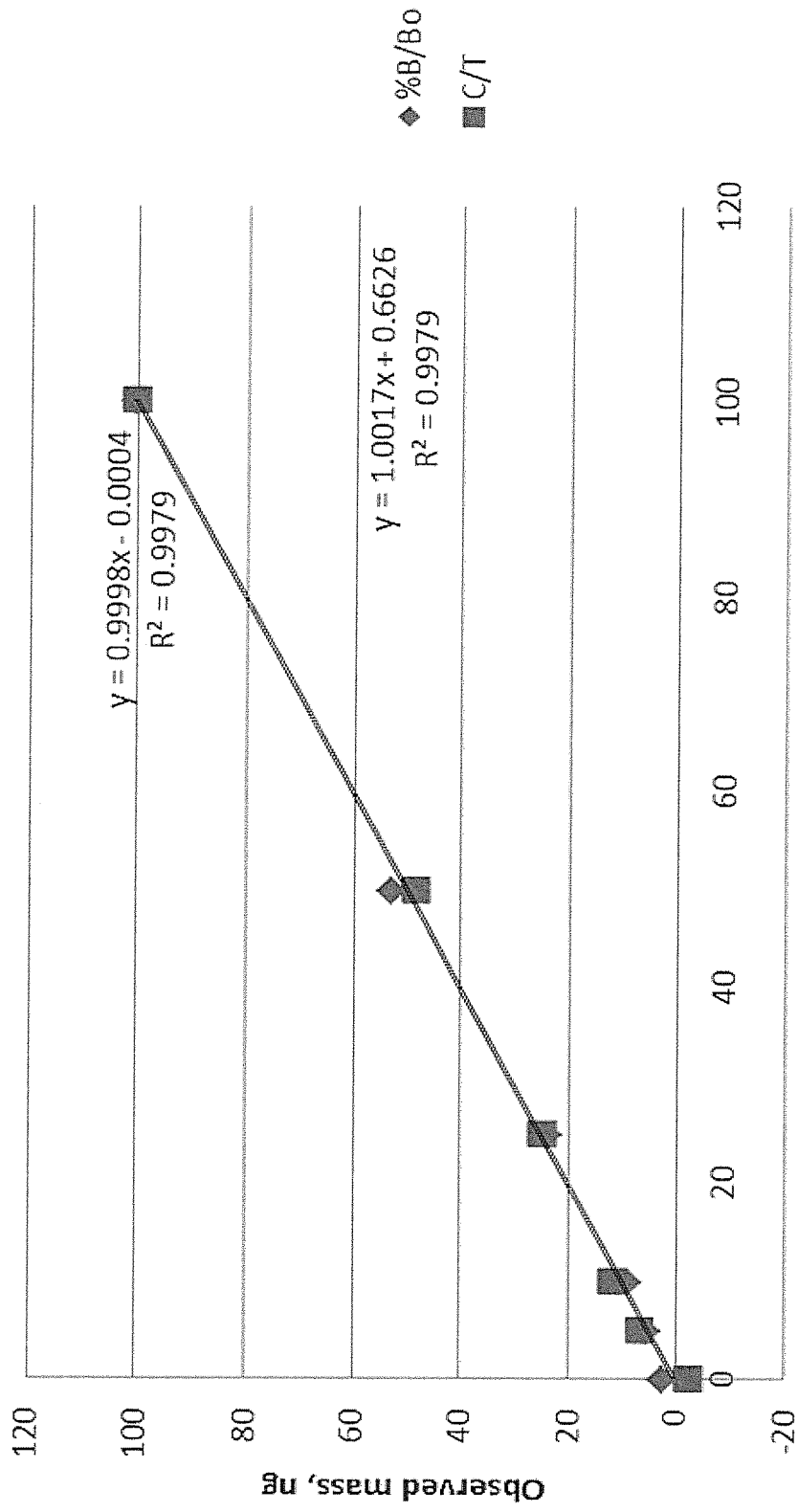
FIG. 3C is a graph showing the observed mass versus the expected mass as was done for the spiked buffer controls and shows good fit.

FIG. 3C is a graph showing the observed mass versus the expected mass as was done for the spiked buffer controls and shows good fit. The standards recovery was calculated by plotting the interpolated results from either % B/Bo versus log mass or C/T versus mass fitted curves (the observed mass) against the mass of 5-FU spiked on the swab (the expected mass).

Figure 3D:
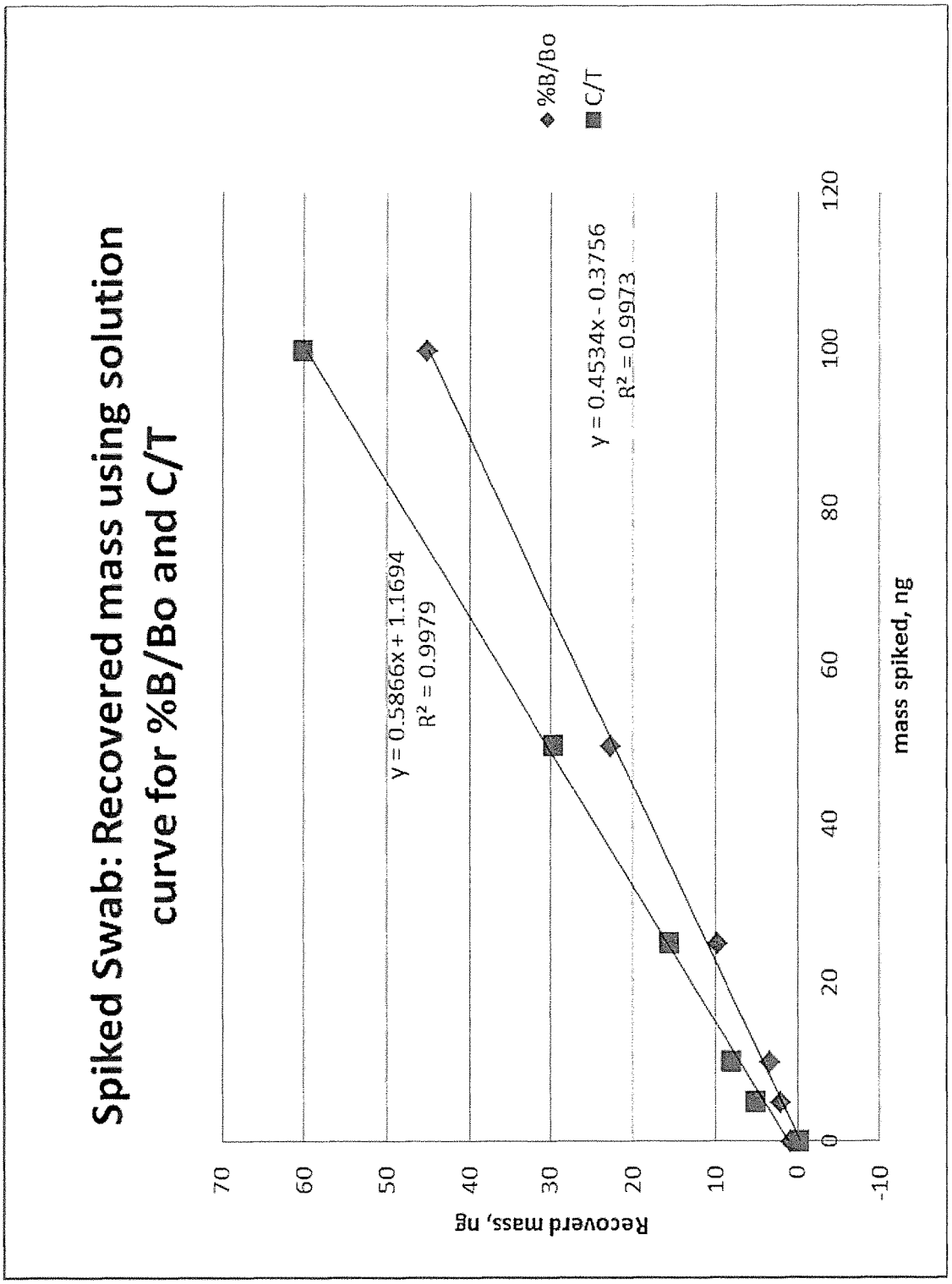
FIG. 3D is a graph showing spiked swab: recovered mass using solution curve for % B/Bo and C/T.

As mentioned above the fitted C/T and % B/Bo curves for the spiked buffer controls were used to calculate the recovered mass for spiked swab control samples. The mass recovered from the spiked swabs was calculated by taking the response of the monitors for the solutions from spiked swabs and using the fitted % B/Bo versus log mass or C/T versus mass fitted curves for spiked sampling buffer solutions to calculate the concentration. FIG. 3D is a graph showing good correlation but incomplete recovery of 5-FU

TABLE I

Visual interpretation of lateral flow monitor response- Most intense line (test-T, control-C) at different spiking levels

| Spiked mass (ng) | Solution | Swab | Wipes Ceramic | Wipes Vinyl | Wipes Composite | Wipes Stainless | Wipes Glass |
|---|---|---|---|---|---|---|---|
| 0 | T to = | T to = | T | T | T to C= | T to = | T= to C= |
| 5 | C= to C | = to C | T= to = | T= to = | = to C= | T to C= | T to = |
| 10 | C | C= to C | T= to C | T= to C | C= to C | = to C= | C= to C |
| 25 | C | C | C | C | C | C | C |
| 50 | C | C | C | C | C | C | C |
| 100 | C | C | C | C | C | C | C |

Table I shows monitor performance using visual interpretation. Monitors were developed with solutions from spiked sampling buffer, spiked swabs and spiked tiles. The results were evaluated by assessing visually which was the most intense line. If the test line was the most intense then T was used and if the control line was the most intense then C was used. If lines were judged as equal then = was used. If the lines were close to equal but the test line was slightly brighter then T= was used If the lines were almost equal but the control was judged slightly brighter then C= was used.

Spiked Swab Control Samples

FIGS. 3A and 3B show % B/Bo and C/T ratio as a function of ng spiked for spiked swabs. FIG. 3A is a graph showing monitor response for solutions from spiked swabs as % B/Bo. Swabs were spiked with increasing masses of 5-FU and the response of the monitors for solutions extracted from these swabs was measured and presented as % B/Bo where B is the response at a given mass and Bo is from the swabs, plot slopes are <1.00. The calculated recovery obtained using the spiked buffer control sample curve gave about 50% recovery for both the % B/Bo and C/T curves, see respective slope values, FIG. 3D.

The LC-MS/MS results also indicated incomplete recovery from the spiked swabs with an average of 86% which agrees well with the slope when the recovery is plotted against mass, Table IIIA, although the values are higher than those from the lateral flow monitor as indicated by slope value <1.00 for swab samples in Table IIIB which correlates the two methods. Visual interpretation indicated that 10 ng 5-FU is detectable since all monitors showed that C= to C by that mass.

Table I shows the visual interpretation of data from spiked swabs which indicates that the control line was more intense than the test line at 10-25 ng spike level.

Spiked Tile Wipe Samples

Figure 4A:
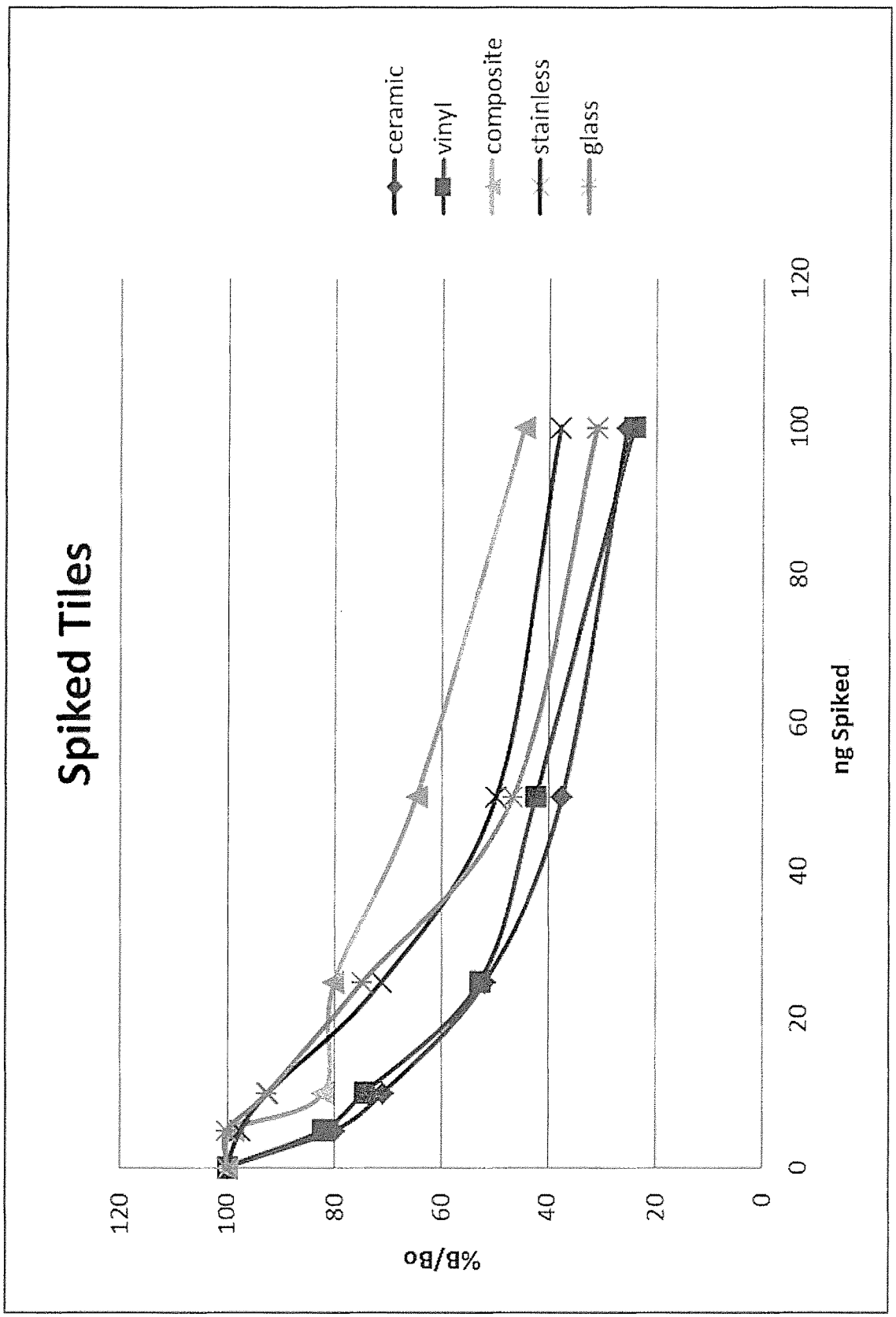
FIG. 4A is a graph showing monitor response for solutions from spiked tiles as % B/Bo.
Figure 4B:
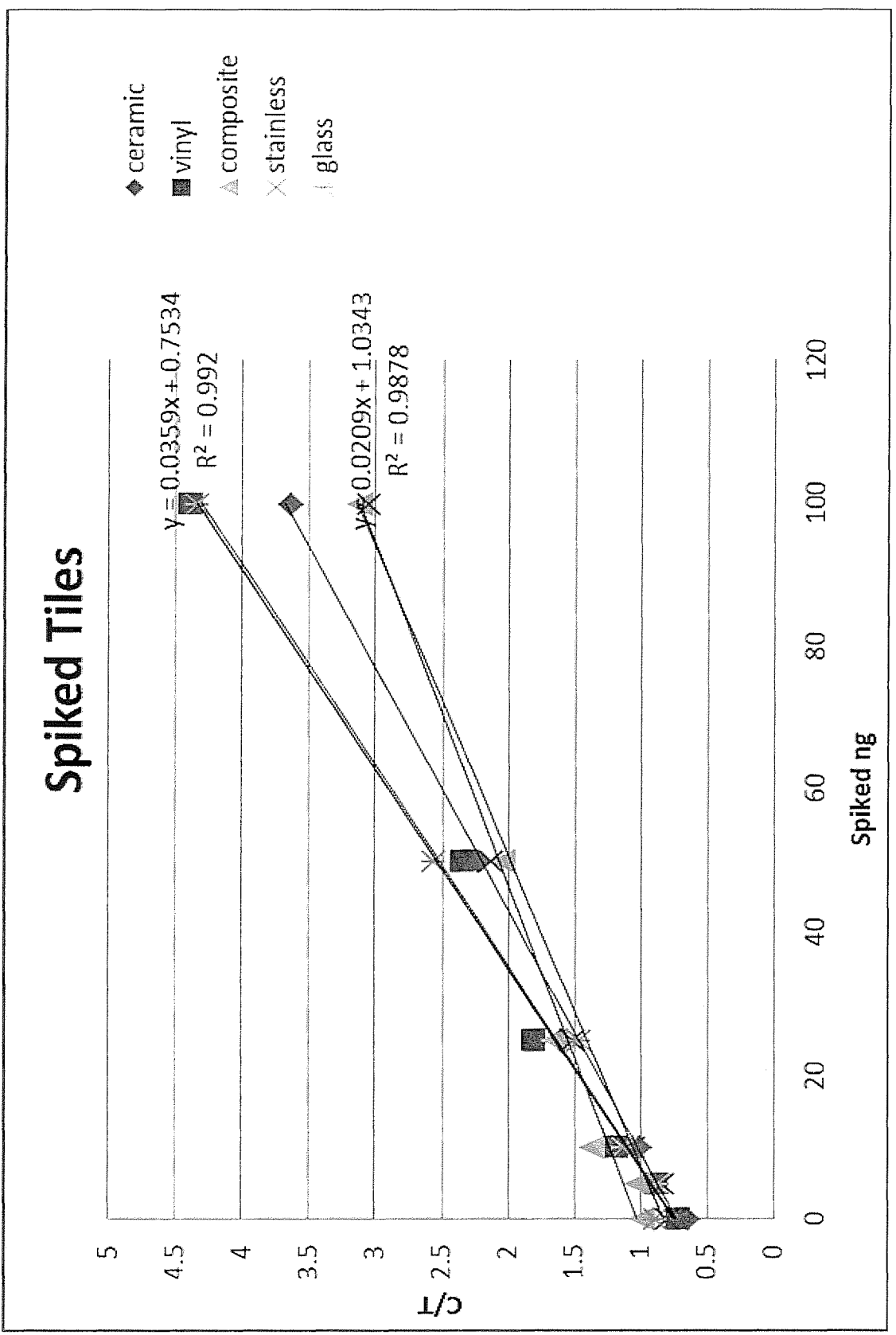
FIG. 4B is a graph showing monitor response for solutions from spiked tiles as C/T Ratio.

The data for the spiked tiles was treated in the same way as the spiked buffer controls and spiked swab controls except that the data for each surface was treated separately. Each value represents an average of 6 lateral flow monitors since there were 3 tiles at each level and 2 lateral flow monitors for each tile. FIGS. 4A and 4B are graphs showing % B/Bo and C/T ratio as a function of ng 5-FU for spiked tile samples. FIG. 4A is a graph showing monitor response for solutions from spiked tiles as % B/Bo. Tiles of 100 cm² area and various surfaces were spiked with increasing masses of 5-FU and the response of the monitors for solutions extracted from swabs used to wipe these tiles was measured and presented as % B/Bo where B is the response at a given mass and Bo is the response at 0 mass.

FIG. 4B is a graph showing monitor response for solutions from spiked tiles as C/T Ratio. Tiles of 100 cm² area and various surfaces were spiked with increasing masses of 5-FU and the response of the monitors for solutions extracted from swabs used to wipe these tiles was measured and presented as C/T ratio where C is the control line intensity and T is the test line intensity. Regression lines for all surface types are shown; however, only the regression equations of the vinyl and the composite are shown on the graph. The regression for the vinyl yielded the highest slope and that for the composite yielded the lowest slope. The slopes for all other surfaces are in between vinyl and composite.

The % B/Bo curves vary from surface to surface with 80% for vinyl and ceramic at 10 ng and 80% between 10 and 25 ng for other surfaces. Tiles were spiked with increasing masses of 5-FU, wiped and the solution was applied to the lateral flow monitors. The response of the monitors was fitted as % B/Bo as a function of log mass and this relationship was used to calculate the observed mass which was plotted against the expected mass and the results are shown in Table IIA.

TABLE IIA

Observed mass versus expected mass
for fitted % B/Bo versus log mass calibration curve

|  | Slope | Intercept | $R^2$ |
| --- | --- | --- | --- |
| Ceramic | 1.0001 | 0.5636 | 0.9983 |
| Composite | 1.3292 | −5.4721 | 0.9357 |
| Glass | 1.0989 | −0.1767 | 0.9835 |
| Stainless | 1.0252 | 1.1418 | 0.9874 |
| Vinyl | 1.0922 | −1.4521 | 0.9866 |

The response of the monitors was fitted as C/T (the ratio of the control line intensity to the test line intensity) as a function of mass and this relationship was used to calculate the observed mass which was plotted against the expected mass and the results are shown in Table IIB.

TABLE IIB

Observed mass versus expected mass for
fitted C/T versus mass calibration curve

|  | Slope | Intercept | $R^2$ |
| --- | --- | --- | --- |
| Ceramic | 0.7467 | 0.0002 | 0.9957 |
| Composite | 0.9986 | −0.0002 | 0.9878 |
| Glass | 1.0012 | −0.0002 | 0.9939 |
| Stainless | 0.9986 | −0.0002 | 0.9867 |
| Vinyl | 0.9993 | 0.0012 | 0.992 |

Tiles were spiked with increasing masses of 5-FU, wiped and the solution was applied to the lateral flow monitors. The fitted % B/Bo versus log mass relationship for the spiked sampling buffer was used with monitor response from spiked tiles to calculate the recovered mass which was plotted against spiked mass, with the results for % B/Bo shown in Table IIC.

TABLE IIC

Recovered mass using fitted solution
% B/Bo versus log mass calibration curve

|  | Slope | Intercept | $R^2$ |
| --- | --- | --- | --- |
| Ceramic | 0.34 | 0.6781 | 0.9977 |
| Composite | 0.1321 | 0.082 | 0.957 |
| Glass | 0.4216 | −2.2471 | 0.9731 |
| Stainless | 0.2721 | −0.1914 | 0.9874 |
| Vinyl | 0.37 | 0.1702 | 0.9913 |

Tiles were spiked with increasing masses of 5-FU, wiped and the solution was applied to the lateral flow monitors. The fitted C/T versus mass relationship for the spiked sampling buffer was used with monitor response from spiked tiles to calculate the recovered mass which was plotted against spiked mass with the results for C/T shown in Table IID.

TABLE IID

Recovered mass using fitted solution
C/T versus mass calibration curve

|  | Slope | Intercept | $R^2$ |
| --- | --- | --- | --- |
| Ceramic | 0.254 | 0.0621 | 0.9957 |
| Composite | 0.2324 | 2.8708 | 0.9878 |
| Glass | 0.7426 | −6.571 | 0.9939 |
| Stainless | 0.3343 | −1.8595 | 0.9867 |
| Vinyl | 0.4008 | −1.2632 | 0.992 |

There is good correlation in spiked tile examples but even lower recovery than with the spiked swab control samples, compare plot slopes against those in FIG. 3D, as would be expected since wiping with swabs would not be expected to be 100% efficient and some surfaces may retain significant amounts of the 5-FU spike (below). Table I shows the visual interpretation for different surfaces which shows all surfaces have the control line more intense than the test line at 25 ng spike levels.

For the spiked tiles, % B/Bo curves varied from surface to surface, as illustrated in FIG. 4A, and indicated 10 ng of 5-FU could be detected on ceramic and vinyl tiles and 10-25 ng on other surfaces. There is good correlation of observed mass with expected mass using the fitted curves for both % B/Bo and C/T for all the surfaces, see Tables IIA, IIB. Calculation of the recovered mass using the spiked buffer control curve indicates generally good correlation but incomplete recovery, see respectively R2 and slope values in Tables IIC and IID, as would be expected from limitations in the wiping technique.

The LC-MS/MS measurements were done on spiked sampling buffer controls and extracts from spiked swab controls and spiked tiles, using the remaining solutions after the lateral flow monitor analyses were complete. The mass measured by the LC-MS/MS was correlated with spiked mass for spiked sampling buffer solutions, spiked swab solutions and spiked the solutions, overall and by tile type. Table IRA shows the correlation of the recovered mass measured from LC-MS/MS with the spiked mass for each type of sample. As mentioned earlier these recoveries are determined using an independent calibration curve prepared by the LC-MS/MS analyst using new standards prepared in sampling buffer, unlike the lateral flow monitors which used the spiked sampling buffer control sample data for calibration. For the surface wipe samples this example shows both an overall correlation and one for each surface type since the surfaces gave different recoveries. LC-MS/MS indicates incomplete recoveries from tile wipe samples as indicated by slope values, shown in Table IIIA.

TABLE IIIA

Correlation of LC-MS/MS measured mass and spiked mass

|  | Slope | Intercept | $R^2$ |
| --- | --- | --- | --- |
| Solution | 1.0185 | −0.2358 | 0.9999 |
| Swab | 0.8276 | 0.5247 | 0.9998 |
| Wipes overall | 0.5039 | −0.5905 | 0.8968 |
| Wipes ceramic | 0.4116 | −0.4191 | 0.9984 |
| Wipes composite | 0.4759 | −0.574 | 0.9994 |
| Wipes glass | 0.3882 | 0.0418 | 0.9998 |
| Wipes stainless | 0.3887 | 0.6229 | 0.9944 |
| Wipes vinyl | 0.7368 | −1.3006 | 0.998 |

The calculated recovered mass measured with the lateral flow monitors was plotted against the recovered mass measured with the LC-MS\MS for spiked sampling buffer solutions, spiked swab solutions and spiked tile solutions, overall and by tile type, with mass ranges 0-100 and 0-25 ng. The recovered mass for the lateral flow monitors used the C/T values from each surface sample type determined with the fitted spiked buffer control curve generated on the same day. For the wipe samples, the correlation was done for (1) all the data including 100 ng spiked and (2) for spiked samples less than 25 ng since those agreed better with the LC-MS/MS results. 100 ng is the only spike level above 25 ng for which a value was determined via LC-MS/MS.

There is good correlation of the recovery values from LC-MS/MS with those calculated from the lateral flow assay, see R2 values in Table IIIB, absolute values of calculated recoveries from the immunoassay are lower, see slope values in Table IIIB are <1.00. The absolute values agree better for mass values 25 ng or less. The exception is stainless steel wipe samples for which there is little difference in agreement. Insufficient LC-MS/MS data was available to allow ranges to be compared for glass wipe samples.

TABLE IIIB

Correlation of Lateral flow monitor recovered mass with LC-MS/MS recovered mass

|  | Slope | Intercept | $R^2$ |
| --- | --- | --- | --- |
| Solution | 0.9923 | 0.5107 | 0.9984 |
| Swab | 0.7341 | 0.6572 | 0.9985 |
| Wipes overall | 0.5894 | 0.3374 | 0.9267 |
| Wipes overall <25 | 0.8192 | −1.0296 | 0.8426 |
| Wipes ceramic | 0.6095 | 0.4502 | 0.9899 |
| Wipes ceramic <25 | 0.9017 | −0.7058 | 0.983 |
| Wipes composite | 0.4365 | 3.1433 | 0.9953 |
| Wipes composite<25 | 0.5233 | 2.7555 | 0.9505 |
| Wipes glass <25 | 1.0748 | −3.6148 | 0.9123 |
| Wipes stainless | 0.9218 | −2.418 | 0.9999 |
| Wipes stainless <25 | 0.9218 | −2.418 | 0.9995 |
| Wipes vinyl | 0.5469 | 0.0382 | 0.9913 |
| Wipes vinyl <25 | 0.8059 | −1.6581 | 0.9888 |

These results show that when the monitors are used with a sampling technique using the cotton swabs as described in this example, 25 ng 5-FU can be detected visually and less than 25 ng can be detected using the electronic reader. The 5-FU detection technique employing surface wiping and lateral flow monitors described in this example provide a sensitivity of 25 ng/100 cm$^2$ (0.25 ng/cm$^2$) or better in a time of 15 minutes or less.

Individual ceramic tile surfaces, 10×10 cm, were spiked with known amounts of paclitaxel, 0-500 ng. The ceramic tile was wiped with a wetted swab and the paclitaxel was extracted from the swab as described for 5-FU. The resulting test solution was applied to the lateral flow assay device and the result was evaluated using both visual and electronic reader techniques. Using the electronic reader, % B/Bo was 70% at 25 ng/ml for spiked solutions and 50 ng/100 cm$^2$ for tile wipe samples. Using visual interpretation, the control line was more intense than the test line at greater than 50 ng/ml for spiked solutions and greater than 50 ng/100 cm$^2$ for the tile wipe samples. PBS-1% Tween was used as a sampling buffer for paclitaxel monitors in this example.

Figure 5A:
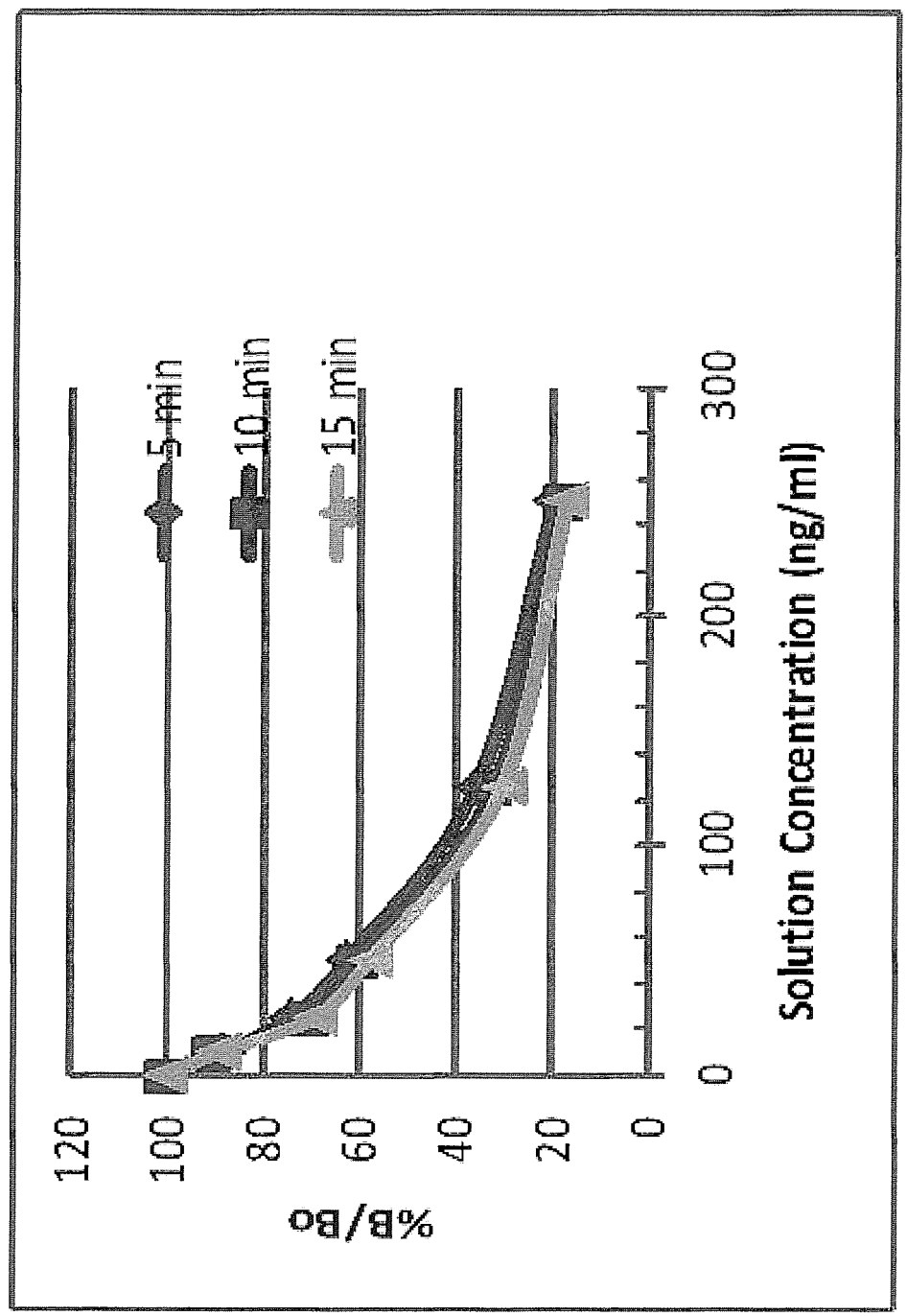
FIG. 5A is a graph showing lateral flow assay monitor response for paclitaxel spiked sampling buffer as % B/Bo.

FIG. 5A is a graph showing lateral flow assay monitor response for paclitaxel spiked sampling buffer as % B/Bo. The sampling buffer was spiked with increasing masses of paclitaxel and the response of the monitors was measured and presented as % B/Bo where B is the response at a given mass and Bo is the response at 0 mass.

Figure 5B:
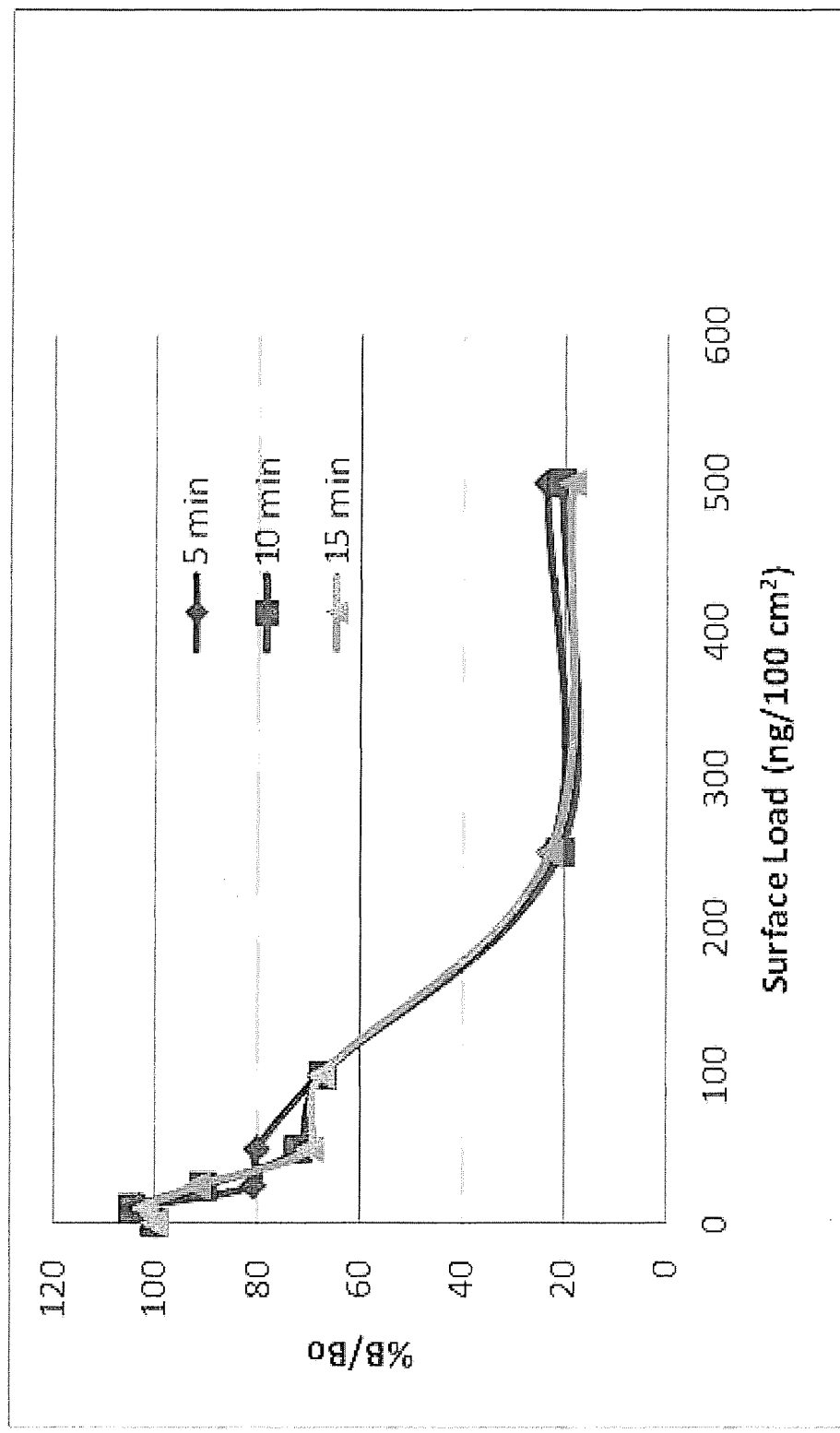
FIG. 5B is a graph showing lateral flow assay monitor response for paclitaxel spiked ceramic tiles as % B/Bo.

FIG. 5B is a graph showing lateral flow assay monitor response for paclitaxel spiked ceramic tiles as % B/Bo. The ceramic tiles spiked with increasing masses of paclitaxel and the response of the monitors was measured and presented as % B/Bo where B is the response at a given mass and Bo is the response at 0 mass.

Figure 5C:
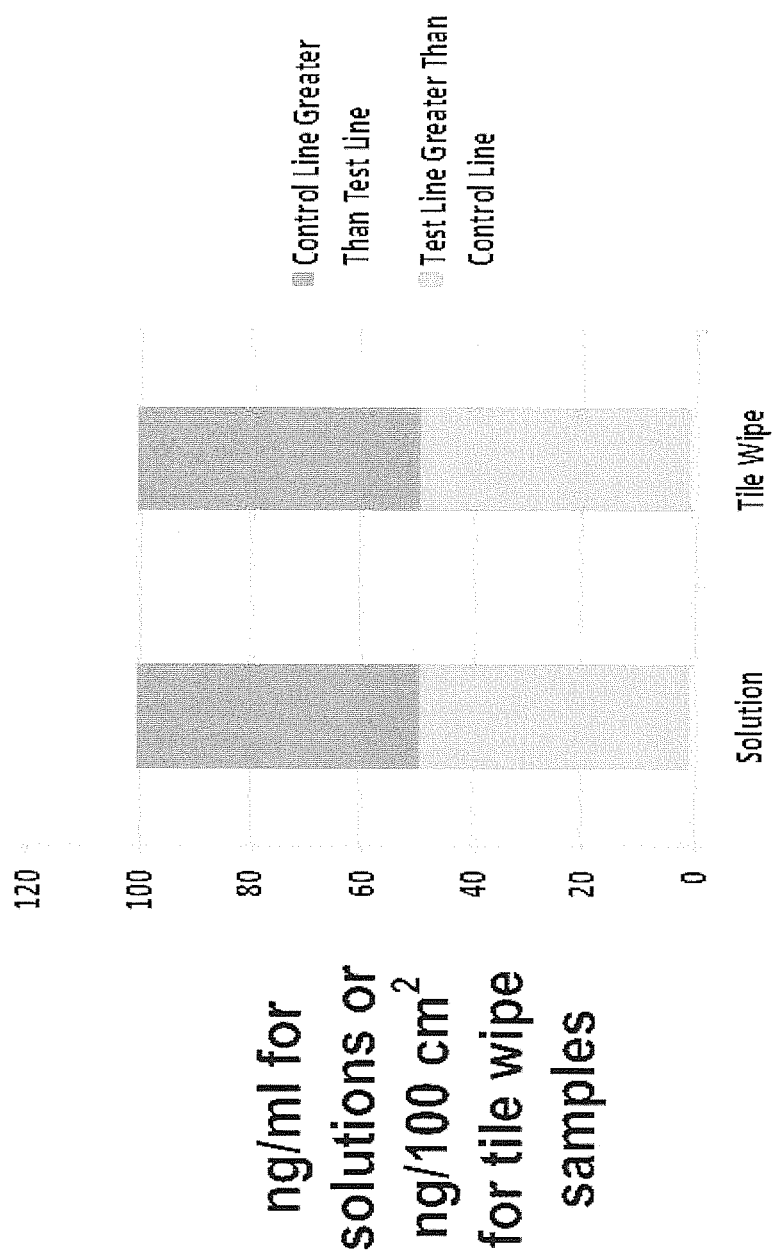
FIG. 5C is a graph showing the detection of various amounts of paclitaxel in spiked buffer or extracted from swabs used to wipe spiked ceramic tiles by visual evaluation of lateral flow assay results.

FIG. 5C is a graph showing the detection of various amounts of paclitaxel in spiked buffer or extracted from swabs used to wipe spiked ceramic tiles by visual evaluation of lateral flow assay results.

The paclitaxel assay detected 0.25 ng/cm$^2$ with the electronic reader and 0.5 ng/cm$^2$ visually in this example.

Individual ceramic tile surfaces, 10×10 cm, were spiked with known amounts of doxorubicin, 0-500 ng. The ceramic tile was wiped with a wetted swab and the paclitaxel was extracted from the swab as described for 5-FU. The resulting test solution was applied to the lateral flow assay device and the result was evaluated using both visual and electronic reader techniques. Using the electronic reader, % B/Bo was 40% at 1 ng/ml for spiked solutions and 80% at 5 ng/100 cm$^2$ for tile wipe samples. Using visual interpretation, the control line was more intense than the test line at greater than 1 ng/ml for spiked solutions and 5 ng/100 cm$^2$ for the tile wipe samples. PBS alone, no Tween, was used as a sampling buffer for doxorubicin monitors in this example. Foam swabs were used.

Figure 6A:
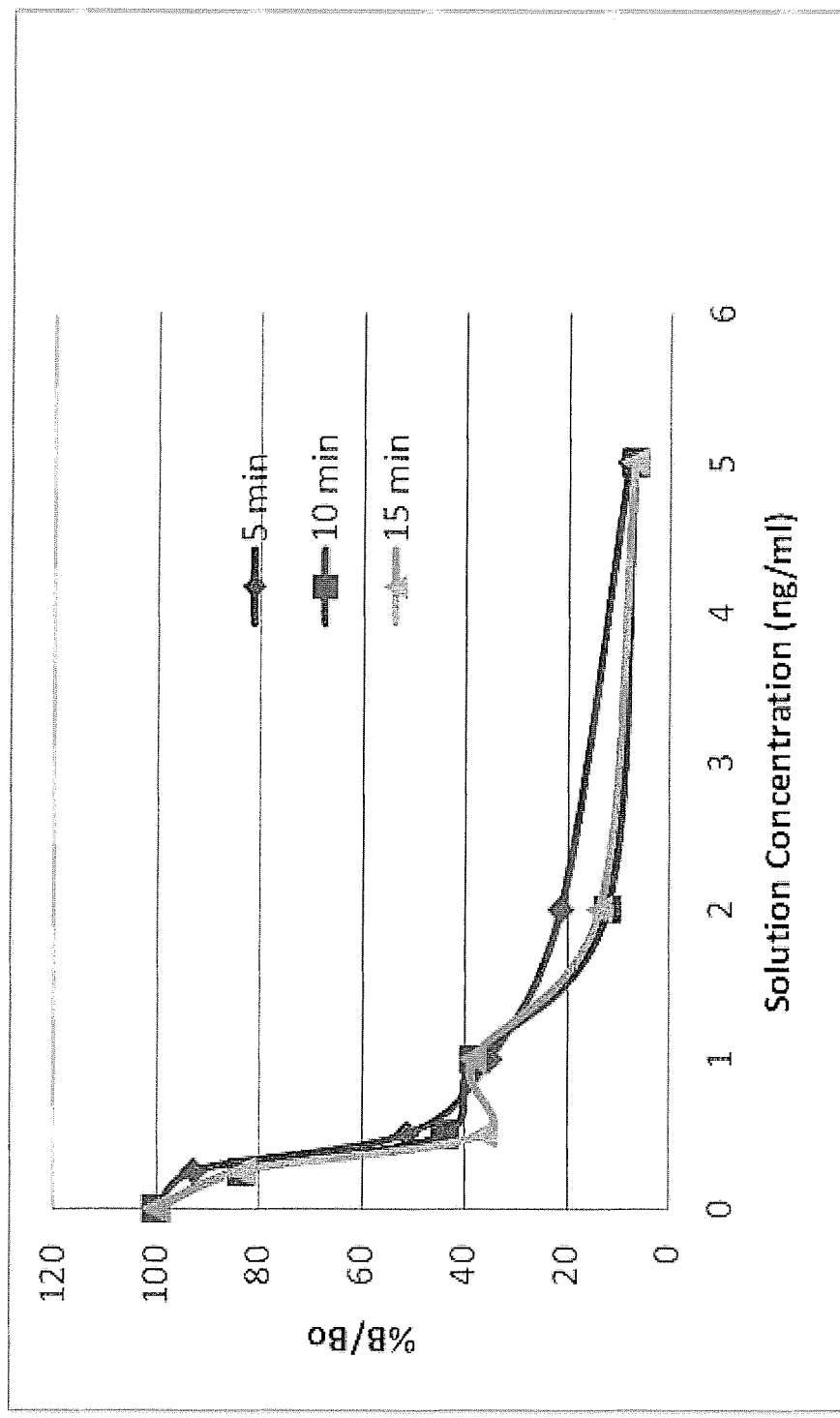
FIG. 6A is a graph showing lateral flow assay monitor response for doxorubicin spiked sampling buffer as % B/Bo.

FIG. 6A is a graph showing lateral flow assay monitor response for doxorubicin spiked sampling buffer as % B/Bo. The sampling buffer was spiked with increasing masses of doxorubicin and the response of the monitors was measured and presented as % B/Bo where B is the response at a given mass and Bo is the response at 0 mass.

Figure 6B:
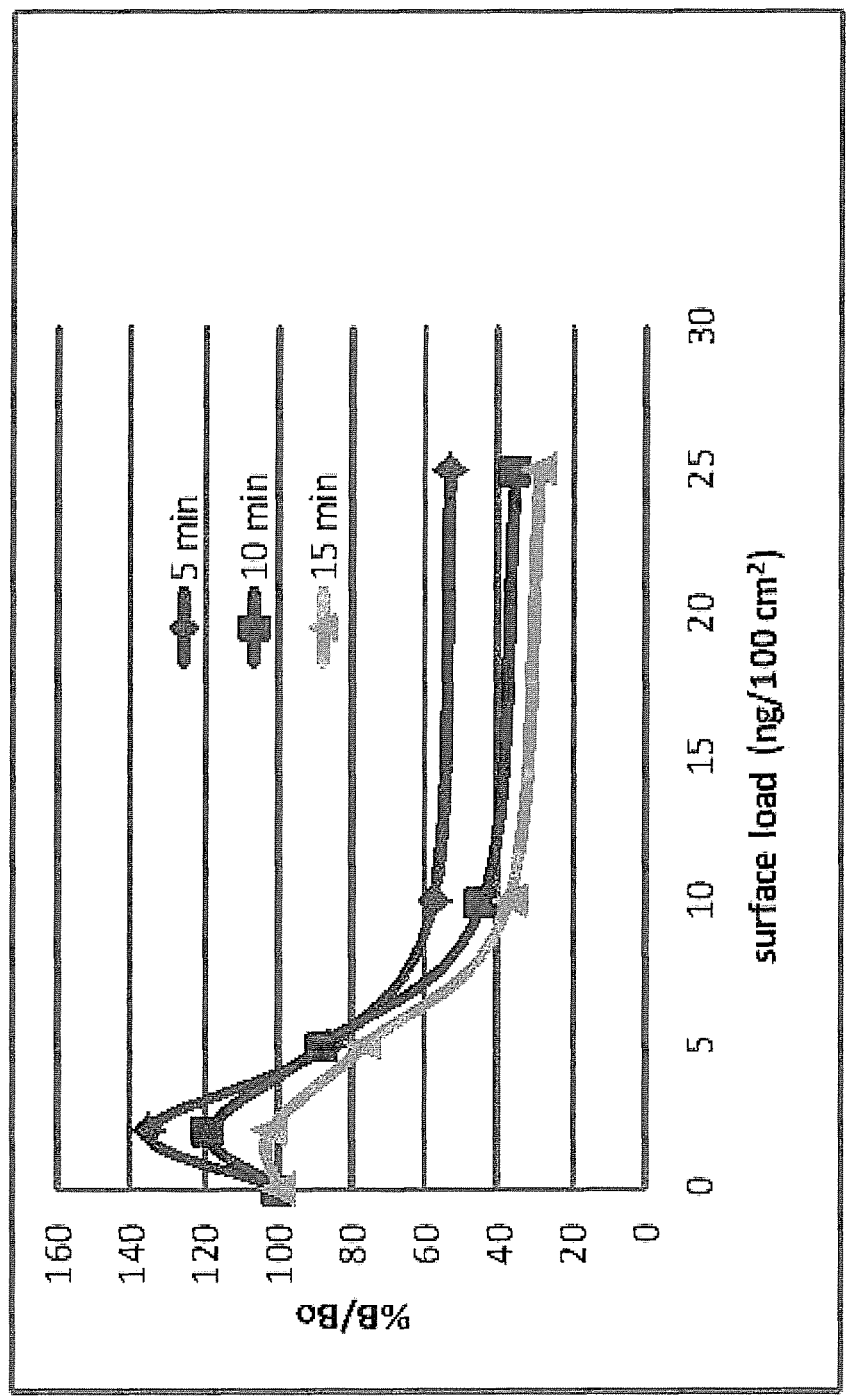
FIG. 6B is a graph showing lateral flow assay monitor response for doxorubicin spiked ceramic tiles as % B/Bo.

FIG. 6B is a graph showing lateral flow assay monitor response for doxorubicin spiked ceramic tiles as % B/Bo. The ceramic tiles spiked with increasing masses of doxorubicin and the response of the monitors was measured and presented as % B/Bo where B is the response at a given mass and Bo is the response at 0 mass.

Figure 6C:
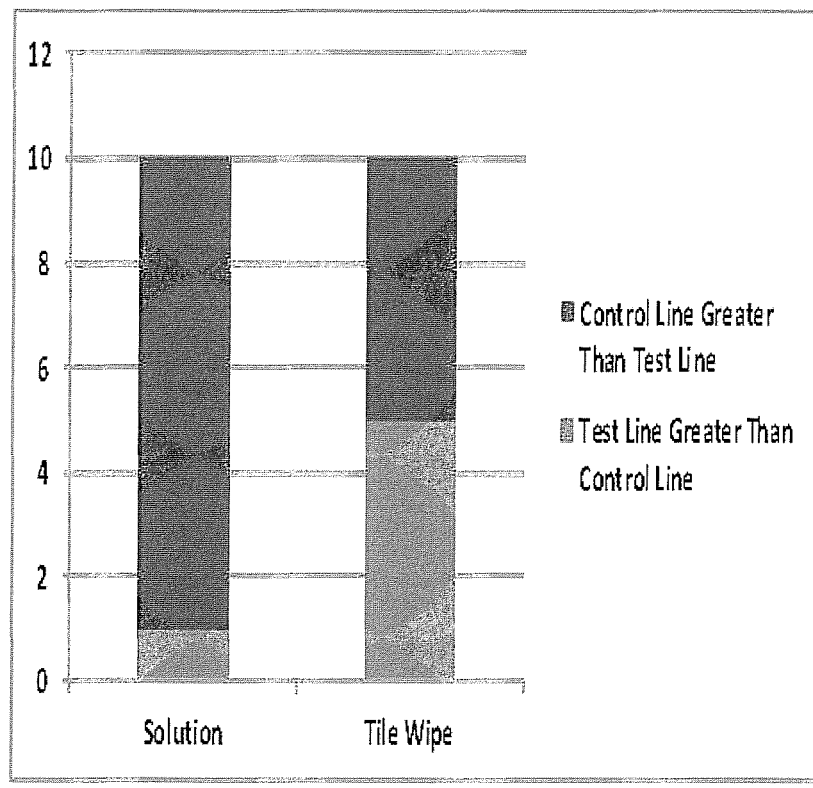
FIG. 6C is a graph showing the detection of various amounts of doxorubicin in spiked buffer or extracted from swabs used to wipe spiked ceramic tiles by visual evaluation of lateral flow assay results.

FIG. 6C is a graph showing the detection of various amounts of doxorubicin in spiked buffer or extracted from swabs used to wipe spiked ceramic tiles by visual evaluation of lateral flow assay results.

The doxorubicin assay detected 0.05-0.1 ng/cm² visually.

Any patents or publications mentioned in this specification are incorporated herein by reference to the same extent as if each individual publication is specifically and individually indicated to be incorporated by reference.

The devices, kits and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for assaying for antineoplastic drug contamination of a surface comprising:
   providing a wetting solution comprising 0.01-10% v/v of a non-ionic surfactant, said wetting solution compatible with an antineoplastic drug and a competitive lateral flow assay;
   providing a solid matrix for reversible absorption of the antineoplastic drug from a surface;
   contacting the solid matrix with the wetting solution, generating an assay matrix;
   contacting the assay matrix and the surface, generating a surface sample;
   contacting the surface sample with a volume of the wetting solution, generating a fluid test sample;
   assaying for the antineoplastic drug in the fluid test sample by a competitive lateral flow assay to produce a detectable assay result, the competitive lateral flow assay comprising:
   a labeled anti-antineoplastic drug antibody to which the antineoplastic drug binds;
   an antineoplastic drug which binds to the labeled anti-antineoplastic drug antibody; and
   a control reagent that binds specifically to the anti-antineoplastic drug antibody; and
   detecting the detectable assay result.

2. The method of claim 1, further comprising comparing the assay result to a standard.

3. The method of claim 1, wherein the antineoplastic drug is selected from the group consisting of: doxorubicin, paclitaxel and 5-fluorouracil.

4. The method of claim 1, wherein the competitive lateral flow assay comprises: providing a lateral flow assay device, the device comprising a conjugate pad, a solid or semi-solid porous support adjacent the conjugate pad, a test zone present on the support and a control zone present on the support, wherein the labeled anti-antineoplastic drug antibody is detectably labeled and diffusibly bound to the conjugate pad, wherein the antineoplastic drug which binds to the detectably labeled anti-antineoplastic drug antibody is non-diffusibly bound to the test zone and the control reagent is non-diffusibly bound to the control zone, and wherein the solid or semi-solid porous support is adjacent a wicking pad that promotes the capillary flow of the fluid test sample along a flow path including the conjugate pad and the solid or semisolid porous support.

5. The method of claim 1, wherein the control reagent is an antibody which binds specifically to the anti-antineoplastic drug antibody.

6. The method of claim 1, wherein detecting the assay result is by visual observation or electronic reader.

7. The method of claim 1, wherein the wetting solution further comprises a buffer and 0.01-10% v/v of an organic solvent.

8. The method of claim 7, wherein the organic solvent is an organic polar protic solvent.

9. The method of claim 1, wherein the surface is a hard surface selected from the group consisting of ceramic, vinyl, composite, stainless steel and glass.

10. A kit for assaying for antineoplastic drug contamination of a surface comprising:
    a wetting solution comprising 0.01-10% v/v of a non-ionic surfactant, said wetting solution compatible with the antineoplastic drug and a competitive lateral flow assay;
    a solid matrix for reversible absorption of the antineoplastic drug from a surface; and
    a competitive lateral flow device comprising: a labeled antineoplastic drug binding agent, a detection reagent; and a control reagent, wherein the antineoplastic drug binding agent is an anti-antineoplastic drug antibody; the detection reagent is an antineoplastic drug which binds to the antineoplastic drug binding agent, and the control reagent binds specifically to the anti-antineoplastic drug antibody.

11. The kit of claim 10, wherein the competitive lateral flow assay device comprises:
    a conjugate pad, a solid or semi-solid porous support adjacent the conjugate pad, a test zone present on the support and a control zone present on the support, wherein the anti-antineoplastic drug antibody is detectably labeled and is diffusibly bound to the conjugate pad, wherein the detection reagent is non-diffusibly bound to the test zone and the control reagent is non-diffusibly bound to the control zone, and wherein the solid or semi-solid porous support is adjacent a wicking pad that promotes the capillary flow of a fluid test sample along a flow path including the conjugate pad and the solid or semi-solid porous support.

12. The kit of claim 10, wherein the control reagent is an antibody which binds specifically to the anti-antineoplastic drug antibody.

13. The kit of claim 10, wherein the wetting solution further comprises a buffer and 0.01-10% v/v of an organic solvent.

14. The kit of claim 13, wherein the organic solvent is an organic polar protic solvent.

15. The kit of claim 10, wherein the surface is a hard surface selected from the group consisting of ceramic, vinyl, composite, stainless steel and glass.

* * * * *